(12) United States Patent
Katagiri et al.

(10) Patent No.: US 11,767,287 B2
(45) Date of Patent: Sep. 26, 2023

(54) COMPOUND AND METHOD FOR PRODUCING THE SAME, RESIN COMPOSITION, RESIN SHEET, MULTILAYER PRINTED WIRING BOARD, AND SEMICONDUCTOR DEVICE

(71) Applicant: MITSUBISHI GAS CHEMICAL COMPANY, INC., Tokyo (JP)

(72) Inventors: Shunsuke Katagiri, Tokyo (JP); Takuya Suzuki, Tokyo (JP); Seiji Shika, Tokyo (JP); Yune Kumazawa, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 17/784,163

(22) PCT Filed: Dec. 9, 2020

(86) PCT No.: PCT/JP2020/045830
§ 371 (c)(1),
(2) Date: Jun. 10, 2022

(87) PCT Pub. No.: WO2021/117760
PCT Pub. Date: Jun. 17, 2021

(65) Prior Publication Data
US 2023/0057045 A1    Feb. 23, 2023

(30) Foreign Application Priority Data
Dec. 11, 2019    (JP) .................. 2019-223931

(51) Int. Cl.
*C07C 69/75*    (2006.01)
*C08G 73/12*    (2006.01)
*H05K 1/02*    (2006.01)

(52) U.S. Cl.
CPC .............. *C07C 69/75* (2013.01); *C08G 73/12* (2013.01); *H05K 1/0271* (2013.01)

(58) Field of Classification Search
CPC ........... H05K 3/389; H05K 2201/0129; H05K 1/0313; H05K 2201/068; H05K 1/03;
(Continued)

(56) References Cited

U.S. PATENT DOCUMENTS 5,196,485 A    3/1993  Mcmonigal et al.
9,188,871 B2    11/2015  Endo et al.
(Continued)

FOREIGN PATENT DOCUMENTS

JP    H6-504314 A    5/1994
JP    H11-246794 A    9/1999
(Continued)

OTHER PUBLICATIONS

ISR for PCT/JP2020/045830, dated Feb. 2, 2021.
(Continued)

*Primary Examiner* — Deborah D Carr
(74) *Attorney, Agent, or Firm* — GREENBLUM & BERNSTEIN, P.L.C.

(57) ABSTRACT

A compound (A) of the present invention is represented by the formula (1): wherein each $R_1$ independently represents a group represented by the formula (2) or a hydrogen atom, and each $R_2$ independently represents a hydrogen atom or a linear or branched alkyl group having 1 to 6 carbon atoms, provided that at least one $R_1$ is a group represented by the formula (2); and wherein -* represents a bonding hand.

13 Claims, 5 Drawing Sheets

(58) Field of Classification Search
CPC .... H05K 1/0271; C07C 69/75; C07C 69/757; C07C 2601/14; C07C 67/08; C08G 73/12; C08G 73/1025; C08L 79/085; C07B 2200/07
See application file for complete search history.

(56) References Cited

U.S. PATENT DOCUMENTS

| | | |
|---|---|---|
| 10,202,493 B2 | 2/2019 | Murakami et al. |
| 2014/0072717 A1 | 3/2014 | Endlish et al. |
| 2019/0281697 A1 | 9/2019 | Abe et al. |

FOREIGN PATENT DOCUMENTS

| | | |
|---|---|---|
| JP | 2014-234500 A | 12/2014 |
| JP | 2015-229734 A | 12/2015 |
| JP | 2017-39894 A | 2/2017 |
| JP | 2018-202690 A | 12/2018 |
| JP | 2019-189757 A | 10/2019 |
| JP | 2019-196444 A | 11/2019 |
| WO | WO 2018/056466 A1 | 3/2018 |

OTHER PUBLICATIONS

Noh et al., "Synthesis and Application of Water-Based Urethane Acrylate Crosslinking Agent Containing Unsaturated Group", Journal of Applied Polymer Science, 78:1216-1223 (2000).
Notice of Reasons for Refusal for JP App. No. 2021-536211, dated Oct. 15, 2021 (w/ translation).

COMPOUND AND METHOD FOR PRODUCING THE SAME, RESIN COMPOSITION, RESIN SHEET, MULTILAYER PRINTED WIRING BOARD, AND SEMICONDUCTOR DEVICE

TECHNICAL FIELD

The present invention relates to a compound and a method for producing the same, a resin composition, a resin sheet, a multilayer printed wiring board, and semiconductor device.

BACKGROUND ART

Due to the downsizing and densification of multilayer printed wiring boards, studies have been actively conducted to make the laminate used for multilayer printed wiring boards thinner. Along with the thinning, the insulation layer also needs to be made thinner, and a resin sheet not containing glass cloth has been demanded. The resin composition used as the material of the insulation layer is mainly a thermosetting resin, and drilling of holes between insulation layers to obtain conduction is generally carried out by laser processing.

Meanwhile, the drilling of holes by laser processing has a problem that the processing time becomes longer as the number of holes in a high density substrate becomes larger. In recent years, therefore, there has been a demand for a resin sheet that enables batch drilling in the exposure and development steps by using a resin composition in which an exposed portion is cured by irradiation of rays of light or the like (exposure step) and an unexposed portion can be removed (development step).

As the method of exposure, a method in which a mercury lamp is used as a light source and the exposure is carried out via a photomask is used. A material which can be suitably exposed in the method using a mercury lamp as a light source has been demanded. In the exposure method using a mercury lamp as a light source, a ghi line (a g-line with a wavelength of 436 nm, an h-line with a wavelength of 405 nm and an i-line with a wavelength of 365 nm) or the like is used, and a general-purpose photo initiator can be selected. Also, in recent years, the introduction of a direct imaging method, in which a pattern is directly drawn on the photosensitive resin composition layer without using a photomask, based on digital data of the pattern, has also been progressing as the exposure method. Since this direct imaging method provides better alignment accuracy than the exposure method using a photomask and produces a highly detailed pattern, the introduction of this method has been progressing, especially for substrates that require the formation of high density wiring. The light source for this method is a monochromatic light source such as a laser, and in particular, a light source with a wavelength of 405 nm (h-line) is used in devices based on the DMD (Digital Micromirror Device) system, which is capable of forming highly detailed resist patterns.

As a development method, alkaline development is employed because a highly detailed pattern can be obtained.

Patent Document 1 describes a resin composition containing a bismaleimide compound (a curable resin) and a photo radical polymerization initiator (a curing agent) as a photosensitive resin composition used for laminates and resin sheets.

Patent Document 2 also describes a resin composition containing a curable resin such as an epoxy resin and a polyvalent carboxy group-containing compound obtained by reacting bismaleimide with a monoamine, and then reacting an acid anhydride. Patent Document 2 further describes a polyvalent carboxy group-containing compound which enables production of a cured product having alkaline developability.

CITATION LIST

Patent Document

Patent Document 1: International Publication No. WO 2018/56466 (A1)
Patent Document 2: Japanese Patent Laid-Open No. 2015-229734

SUMMARY OF INVENTION

Technical Problem

However, in Patent Document 1, a bismaleimide compound is used as a curable resin, but since the maleimide compound normally has poor light transmissivity, when the maleimide compound is contained, light does not reach the photo initiator sufficiently, the photo initiator has difficulty generating radicals, and its reactivity is very low. Therefore, in Patent Document 1, the maleimide compound is cured by additional heating before development, and highly detailed resist patterns cannot be obtained because heating is performed. Since originally, the resin composition described in Patent Document 1 does not have sufficient alkaline developability, an unexposed resin composition remains even after development. This also suggests that in Patent Document 1, a highly detailed resist pattern cannot be obtained, and the resin composition cannot be used for production of high density printed wiring boards.

In addition, for obtaining the polyvalent carboxy group-containing compound described in Patent Document 2, it is necessary to react bismaleimide with a monoamine and then react an acid anhydride, so that the process is complicated. In addition, an aromatic amine compound is used as the monoamine, and therefore the polyvalent carboxy group-containing compound contains an amide group having an aromatic ring in the structure thereof. Thus, the polyvalent carboxy group-containing compound is poor in light transmissivity, hinders photocuring reaction, and is therefore difficult to use for photosensitive resin compositions in reality.

Accordingly, the present invention has been made in view of such problems of the related art, and an object thereof is to provide a compound which does not inhibit a photocuring reaction in an exposure step and is capable of imparting excellent alkaline developability in a development step when used for production of a multilayer printed wiring board, a resin composition containing the compound, a resin sheet, a multilayer printed wiring board, and a semiconductor device.

Solution to Problem

As a result of intensive studies, the present inventors have found that by using a specific carboxyl group-containing compound in an exposure step and a development step in the production of a multilayer printed wiring board, a cured product can be suitably obtained without inhibiting a photocuring reaction, and excellent alkaline developability can be imparted to a resin composition, thereby completing the present invention.

More specifically, the present invention includes the following contents.

[1] A compound (A) represented by the following formula (1):

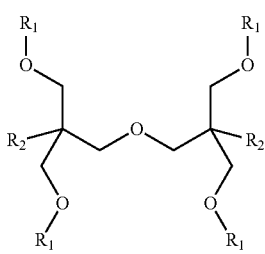

wherein each $R_1$ independently represents a group represented by the following formula (2) or a hydrogen atom, and each $R_2$ independently represents a hydrogen atom or a linear or branched alkyl group having 1 to 6 carbon atoms, provided that at least one $R_1$ is a group represented by the following formula (2); and

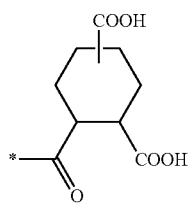

wherein -* represents a bonding hand.

[2] The compound (A) according to [1], wherein at least one $R_1$ is a group represented by the following formula (3):

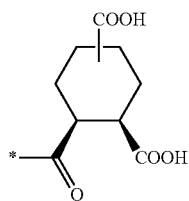

wherein -* represents a bonding hand.

[3] A method for producing the compound (A) according to [1] or [2], containing a step of reacting an alcohol compound represented by the following formula (4) with an acid anhydride represented by the following formula (5):

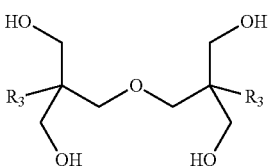

wherein each $R_3$ independently represents a hydrogen atom, or a linear or branched alkyl group having 1 to 6 carbon atoms.

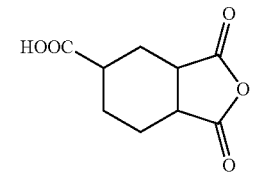

[4] The production method according to [3], wherein the acid anhydride represented by the formula (5) includes an acid anhydride represented by the following formula (6):

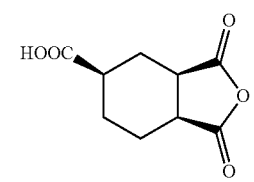

[5] The production method according to [3] or [4], wherein the reaction is carried out in the absence of a catalyst.

[6] The production method according to any one of [3] to [5], wherein the reaction is performed in at least one solvent selected from the group consisting of a halogen solvent, a ketone solvent, and an ester solvent.

[7] The production method according to [6], wherein the solvent is at least one selected from the group consisting of dichloromethane, methyl ethyl ketone, butyl acetate, γ-butyrolactone, and propylene glycol monomethyl ether acetate.

[8] A resin composition containing the compound (A) according to [1] or [2].

[9] The resin composition according to [8], further containing a bismaleimide compound (B) containing a constituent unit represented by the following formula (7) and maleimide groups at both ends of the molecular chain:

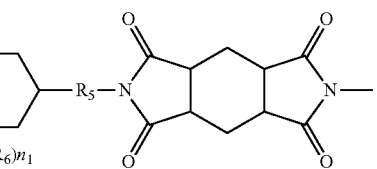

wherein $R_4$ represents a linear or branched alkylene group having 1 to 16 carbon atoms, or a linear or branched alkenylene group having 2 to 16 carbon atoms; $R_5$ represents a linear or branched alkylene group having 1 to 16 carbon atoms, or a linear or branched alkenylene group having 2 to 16 carbon atoms; each $R_6$ independently represents a hydrogen atom, a linear or branched alkyl group having 1 to 16 carbon atoms, or a linear or branched alkenyl group having 2 to 16 carbon atoms; and each $n_1$ independently represents an integer of 1 to 10.

[10] The resin composition according to [8] or [9], further containing at least one maleimide compound (C) selected from the group consisting of a compound represented by the following formula (8), a compound represented by the following formula (9), a compound represented by the following formula (10), a compound represented by the following formula (11), a compound represented by the following formula (12), and a compound represented by the following formula (13):

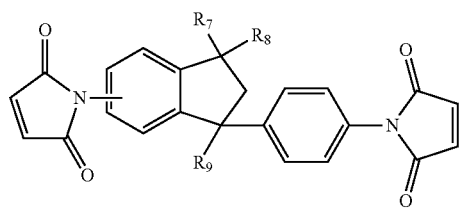
(8)

wherein $R_7$, $R_8$, and $R_9$ each independently represent a hydrogen atom, or a linear or branched alkyl group having 1 to 8 carbon atoms and optionally having a substituent;

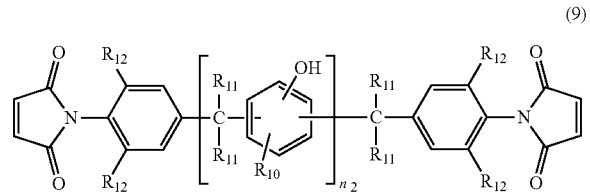
(9)

wherein $R_{10}$, $R_{11}$, and $R_{12}$ each independently represent a hydrogen atom, a hydroxyl group, or a linear or branched alkyl group having 1 to 6 carbon atoms and optionally having a substituent; and $n_2$ is an integer of 1 to 10;

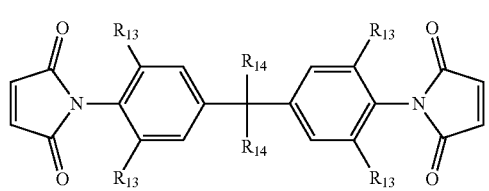
(10)

wherein each $R_{13}$ independently represents a hydrogen atom, a methyl group or an ethyl group, and each $R_{14}$ independently represents a hydrogen atom or a methyl group;

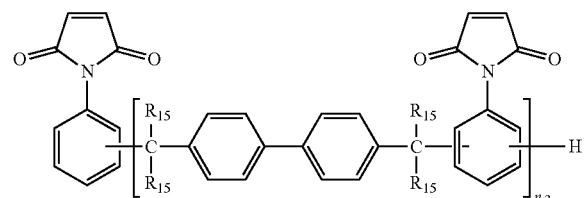
(11)

wherein each $R_{15}$ independently represents a hydrogen atom or a methyl group; and $n_3$ is an integer of 1 to 10;

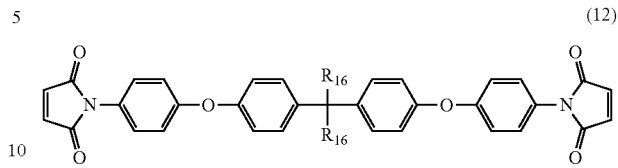
(12)

wherein each $R_{16}$ independently represents a hydrogen atom, a methyl group or an ethyl group; and

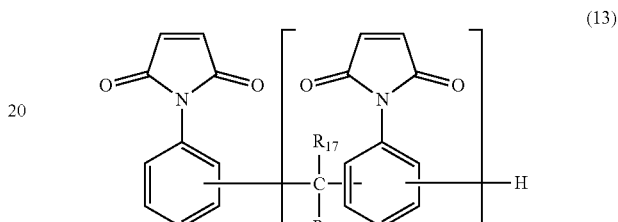
(13)

wherein each $R_{17}$ independently represents a hydrogen atom or a methyl group; and $n_4$ is an integer of 1 to 10.

[11] The resin composition according to any one of [8] to [10], further containing a photo initiator (D).

[12] The resin composition according to [11], wherein the photo initiator (D) contains a compound represented by the following formula (14):

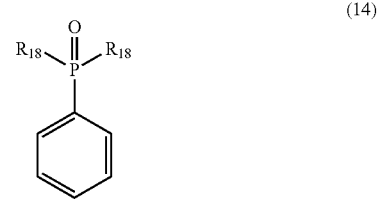
(14)

wherein each $R_{18}$ independently represents a group represented by the following formula (15) or a phenyl group; and

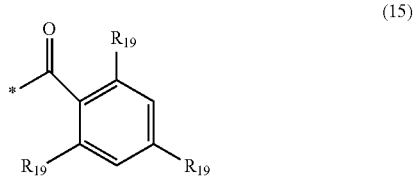
(15)

wherein -* represents a bonding hand, and each $R_{19}$ independently represents a hydrogen atom or a methyl group.

[13] A resin sheet containing a support; and a resin layer disposed on one surface or both surfaces of the support, wherein the resin layer contains the resin composition according to any of [8] to [12].

[14] The resin sheet according to [13], wherein the resin layer has a thickness of 1 to 50 μm.

[15] A multilayer printed wiring board containing an insulation layer; and a conductor layer formed on one surface or both surfaces of the insulation layer, wherein the conductor layer contains the resin composition according to any of [8] to [12].

[16] A semiconductor device containing the resin composition according to any of [8] to [12].

Advantageous Effects of Invention

According to the present invention, it is possible to provide a compound capable of suitably obtaining a cured product without inhibiting a photocuring reaction and imparting excellent alkaline developability to a resin composition by using a compound containing a specific carboxyl group in an exposure step and a development step in the production of a multilayer printed wiring board, a resin composition containing the compound, a resin sheet, a multilayer printed wiring board, and a semiconductor device.

DESCRIPTION OF EMBODIMENTS

Figure 1:
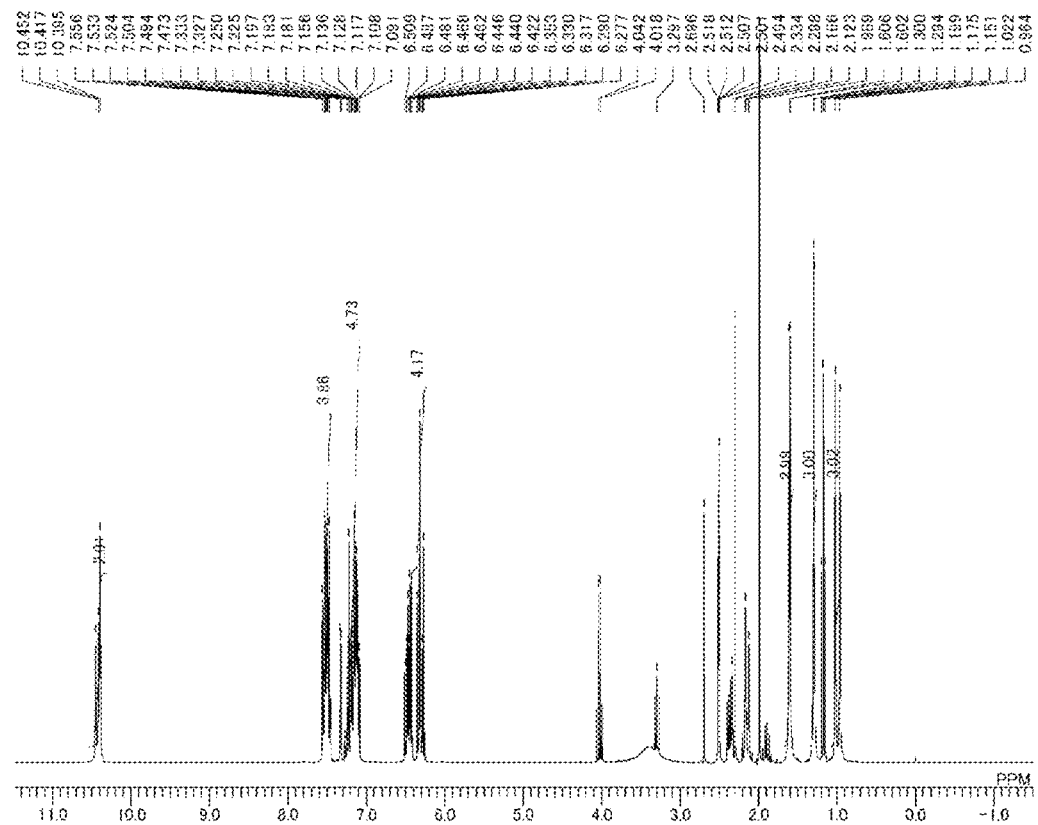
FIG. 1 is a $^1$H-NMR chart of an amic acid compound (MA-TMDA).

Hereinafter, an embodiment for carrying out the present invention (hereinafter, referred to as the "present embodiment") will be described in detail. The present embodiment described below is only illustrative of the present invention and is not intended to limit the present invention to the contents of the following description. The present invention can be carried out with appropriate modifications falling within the gist of the invention.

Note that, in the present specification, the term "(meth) acryloxy" refers to both "acryloyloxy" and "methacryloxy" corresponding thereto, the term "(meth)acryl" refers to both "acryl" and "methacryl" corresponding thereto. Also, in the present embodiment, "resin solid content" or "resin solid content in a resin composition" refers to components in a resin composition excluding a compound (A), a photo initiator (D), an additive agent, a solvent, and a filler unless otherwise noted, and "100 parts by mass of resin solid content" refers to the total of components in a resin composition excluding a compound (A), a photo initiator (D), an additive agent, a solvent, and a filler being 100 parts by mass.

The compound (A) of the present embodiment will be described.

[Compound (A)]

The compound (A) (also referred to as component (A)) of the present embodiment is represented by the formula (1):

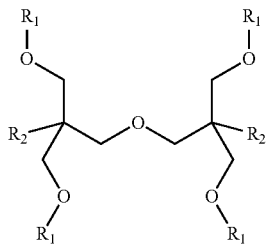

In the formula (1), each $R_1$ independently represents a group represented by the formula (2) or a hydrogen atom, and each $R_2$ independently represents a hydrogen atom or a linear or branched alkyl group having 1 to 6 carbon atoms, provided that at least one $R_1$ is a group represented by the formula (2).

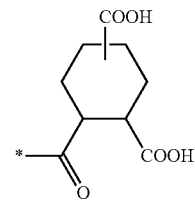

In the formula (2), -* represents a bonding hand with an oxygen atom (O) directly bonded to $R_1$ in the formula (1).

In the present embodiment, by using the compound (A) in an exposure step and a development step in the production of the multilayer printed wiring board, a cured product can be suitably obtained without inhibiting the photocuring reaction, and excellent alkaline developability can be imparted to the resin composition in an unexposed portion even after exposure. The reason for this is not certain, but the present inventors estimate it as follows. That is, in the exposure step in the production of the multilayer printed wiring board, the compound (A) does not have a functional group involved in the photocuring reaction in the exposure step and does not inhibit the photocuring reaction. In addition, the compound (A) does not have a backbone that inhibits light transmissivity and also has very excellent light transmissivity. Therefore, even when the compound (A) is contained, photopolymerization proceeds, and a cured product can be suitably obtained. Since the compound (A) is not involved in the photocuring reaction, the compound (A) can be present in the resin composition in the unexposed portion. Therefore, when the alkaline developing solution flows into an unexposed portion in the development step, the alkaline component in the alkaline developing solution and the carboxy group in the compound (A) can suitably form a salt and water-solubility is improved. Thus, alkaline developability is improved. In addition, since the compound (A) has a plurality of carboxy groups, it is presumed that excellent alkaline developability can be imparted.

The compound (A) has a transmittance of 5% or more when a N-methylpyrrolidone solution containing the compound (A) at 1% by mass is prepared and the transmittance of the N-methylpyrrolidone solution containing the compound (A) at 1% by mass is measured using an active energy ray including a wavelength of 365 nm (i-line). Such a compound (A) exhibits very excellent light transmissivity. In addition, the compound (A) has a transmittance of 5% or more when the transmittance of a N-methylpyrrolidone solution containing the compound (A) at 1% by mass is measured using an active energy ray including a wavelength of 405 nm (h-line). Even in this case, very excellent light transmissivity is exhibited. When such a compound (A) is used, for example, upon producing a printed wiring board having a highly dense and highly detailed wiring formation (pattern) using the direct imaging method, for example, the photo radical reaction of the maleimide occurs efficiently even when an active energy ray including a wavelength of 405 nm (h-line) is used. The transmittance at a wavelength of 365 nm (i-line) is preferably 8% or more, more preferably 10% or more, still more preferably 20% or more, even more preferably 30% or more, and furthermore preferably 40% or more because a resin composition that is superior in photocurability can be obtained. The transmittance at a wavelength of 405 nm (h-line) is preferably 8% or more, more preferably 10% or more, still more preferably 20% or more, even more preferably 30% or more, and furthermore preferably 40% or more because a resin composition that is superior in photocurability can be obtained. The upper limit of each of the transmittance at a wavelength of 365 nm (i-line) and the transmittance at a wavelength of 405 nm (h-line) is, for example, 99.9% or less.

In the compound (A), in the formula (1), each $R_1$ independently represents a group represented by the formula (2) or a hydrogen atom. $R_1$ preferably contains two or more groups represented by the formula (2), more preferably contains three or more groups represented by the formula (2), and still more preferably all $R_1$s are groups represented by the formula (2) because superior alkaline developability can be imparted. In the group represented by the formula (2), when the position of the carbonyl group with respect to the cyclohexane ring is position 1, as long as the carboxyl group is bonded to position 2 with respect to the carbonyl group, the other carboxyl group may be bonded to any of positions 3 to 6 in the cyclohexane ring. Further, in the group represented by the formula (2), since the structure of the carbonyl group bonded to the cyclohexane ring and the two carboxyl groups has a three dimensional structure, the compound (A) is present as a cis form, a trans form, and a mixture of the cis form and the trans form. That is, the compound (A) may be a single compound or a mixture containing two or more isomers thereof.

In the formula (1), at least one $R_1$ is preferably a group represented by the formula (3) because superior alkaline developability can be imparted. That is, in the group represented by the formula (3), the steric structure of the carbonyl group bonded to position 1 of the cyclohexane ring and the carboxyl group at position 2 is preferably a cis form. The steric structure of the other carboxyl group may be a cis form or a trans form. $R_1$ preferably contains two or more groups represented by the formula (3), more preferably contains three or more groups represented by the formula (3), and still more preferably all $R_1$s are groups represented by the formula (3) because further excellent alkaline developability can be imparted. The reason why superior alkaline developability can be imparted when at least one $R_1$ is a group represented by the formula (3) is not clear, but the present inventors presume as follows. That is, it is presumed that when the carbonyl group bonded to position 1 and the carboxyl group bonded to position 2 are cis forms, the carboxyl group at position 2 and the alkali component in the alkali developer can have a three dimensional structure which is likely to form a salt in the resin composition, and thus the water solubility is further improved and the inflow of the alkaline developing solution into the resin composition is further promoted.

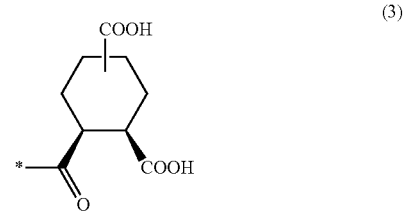

(3)

In the formula (3), -* represents a bonding hand with an oxygen atom (O) directly bonded to $R_1$ in the formula (1).

Each $R_2$ independently represents a hydrogen atom, or a linear or branched alkyl group having 1 to 6 carbon atoms.

Examples of the linear or branched alkyl group having 1 to 6 carbon atoms include a methyl group, an ethyl group, a n-propyl group, an isopropyl group, a n-butyl group, a 2-butyl group, an isobutyl group, a tert-butyl group, a n-pentyl group, a 2-pentyl group, a tert-pentyl group, a 2-methylbutyl group, a 3-methylbutyl group, a 2,2-dimethylpropyl group, a n-hexyl group, a 2-hexyl group, a 3-hexyl group, a 2-methylpentyl group, a 3-methylpentyl group, a 4-methylpentyl group, and a 2-methylpentan-3-yl group.

$R_2$ is preferably a linear alkyl group having 1 to 6 carbon atoms, more preferably a methyl group, an ethyl group, a n-propyl group, a 2-butyl group, an iso-butyl group, a tert-butyl group, and a n-pentyl group, and still more preferably a methyl group, an ethyl group, and a n-propyl group, from the viewpoint of exhibiting good solubility in a solvent.

The compound (A) is preferably a compound represented by the formula (16) or a compound represented by the formula (17), and more preferably a compound represented by the formula (17), from the viewpoint of imparting superior alkaline developability and further exhibiting good solubility in a solvent.

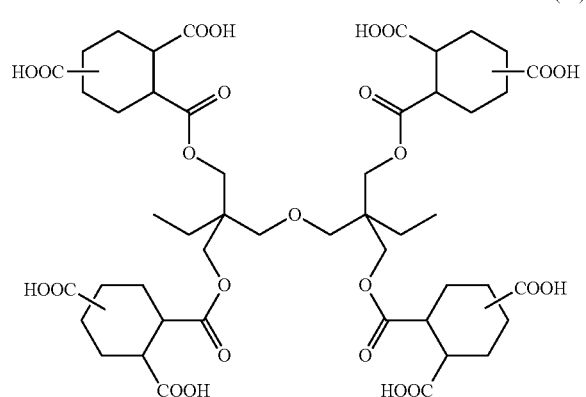

(16)

-continued

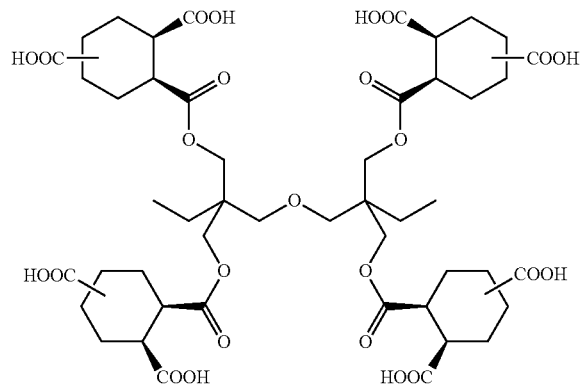

(17)

[Method for Producing Compound (A)]

The compound (A) can be produced by a known method, and can be obtained, for example, by including a step of subjecting an alcohol compound represented by the formula (4) and an acid anhydride (cyclohexane-1,2,4-tricarboxylic acid-1,2-anhydride) represented by the formula (5) to an esterification reaction. In the acid anhydride represented by the formula (5), since the structure of two carbonyl group bonded to the cyclohexane ring and one carboxyl group has a three dimensional structure, the compound (A) is present as a cis form, a trans form, and a mixture of the cis form and the trans form. That is, the acid anhydride represented by the formula (5) may be a single compound or a mixture containing two or more isomers thereof.

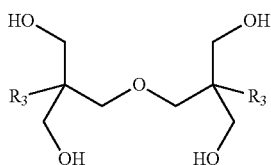

(4)

In the formula (4), each $R_3$ independently represents a hydrogen atom, or a linear or branched alkyl group having 1 to 6 carbon atoms.

As the linear or branched alkyl group having 1 to 6 carbon atoms, $R_2$ in the formula (1) can be referred to, including its preferred embodiment.

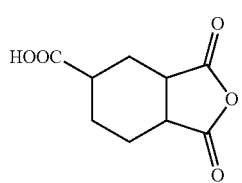

(5)

Examples of the alcohol compound represented by the formula (4) include ditrimethylolethane, ditrimethylolpropane, ditrimethylolbutane, ditrimethylolpentane, 2,2'-(oxybis(methylene))bis(propane-1,3-diol), 2,2'-(oxybis(methylene))bis(2-methylpropane-1,3-diol), and 2-((2,2-bis(hydroxymethyl)butoxy)methyl)-2-methylpropane-1,3-diol.

The acid anhydride represented by the formula (5) preferably contains an acid anhydride represented by the formula (6) (cis,cis-cyclohexane-1,2,4-tricarboxylic acid-1,2-anhydride) because excellent alkaline developability can be imparted when a cured product is produced by using the compound (A). That is, in the acid anhydride represented by the formula (6), when the positions of the carbonyl groups with respect to the cyclohexane ring are position 1 and position 2, the steric structure of the carbonyl group bonded to position 4 with respect to the carbonyl group and the two carbonyl groups is preferably a cis form.

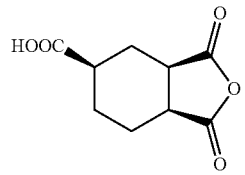

(6)

The esterification reaction can be carried out in a solvent or without a solvent. The solvent is not particularly limited as long as it does not react with an alcohol compound and an acid anhydride.

Examples of such solvents include halogen solvents such as dichloromethane, chloroform, dichloroethane, and chlorobenzene; aprotic polar solvents such as dimethylformamide, dimethylacetamide, dimethylsulfoxide, tetrahydrofuran, dioxane, and acetonitrile; ketone solvents such as acetone, methyl ethyl ketone, methyl isobutyl ketone, cyclopentanone, and cyclohexanone; cellosolve solvents such as 2-ethoxyethanol and propylene glycol monomethyl ether; aliphatic alcohol solvents such as methanol, ethanol, propanol, isopropanol, and butanol; aromatic group-containing phenol solvents such as phenol and cresol; ester solvents such as ethyl lactate, methyl acetate, ethyl acetate, butyl acetate, isoamyl acetate, methyl methoxypropionate, methyl hydroxyisobutyrate, γ-butyrolactone, and propylene glycol monomethyl ether acetate; and aromatic hydrocarbon solvents such as toluene and xylene. One of these solvents can be used, or two or more of these solvents can be appropriately mixed and used.

Among these, halogen solvents, aprotic polar solvents, ketone solvents, and ester solvents are preferable because they can sufficiently dissolve alcohol compounds and acid anhydrides.

The halogen solvent is preferably dichloromethane. The aprotic polar solvent is preferably dimethylacetamide. The ketone solvent is preferably methyl ethyl ketone. The cellosolve solvent is preferably propylene glycol monomethyl ether. The ester solvent is preferably butyl acetate, γ-butyrolactone, or propylene glycol monomethyl ether acetate.

The amount used in the case of using a solvent is usually 20 to 2000 parts by mass based on a total of 100 parts by mass of the alcohol compound and the acid anhydride.

The esterification reaction may be carried out in the absence or presence of a catalyst.

In the case of using a catalyst, examples of the catalyst include acidic compounds such as hydrochloric acid, sulfuric acid, methanesulfonic acid, trifluoromethanesulfonic acid, paratoluenesulfonic acid, nitric acid, trifluoroacetic acid, and trichloroacetic acid; metal hydroxides such as sodium hydroxide, potassium hydroxide, calcium hydroxide, and magnesium hydroxide; amine compounds such as triethylamine, tripropylamine, diisopropylethylamine, and tributylamine; aliphatic amines having aromatic rings such as aniline, N-methylaniline, N,N-dimethylaniline, and benzylamine; heterocyclic compounds such as pyridine, 4-dimethylaminopyridine, 1,8-diazabicyclo[5.4.0]undec-7-ene, imidazole, triazole, and tetrazole; quaternary ammonium salts such as tetramethylammonium hydroxide, tetraethylammonium hydroxide, tetrapropylammonium hydroxide, tetrabutylammonium hydroxide, trimethylethylammonium hydroxide, trimethylpropylammonium hydroxide, trimethylbutylammonium hydroxide, trimethylcetylammonium hydroxide, trioctylmethylammonium hydroxide, tetramethylammonium chloride, tetramethylammonium bromide, tetramethylammonium iodide, tetramethylammonium acetate, and trioctylmethylammonium acetate; orthotitanic acids such as tetraethyl orthotitanate and tetramethyl orthotitanate; and metal soaps such as tin octylate, cobalt octylate, zinc octylate, manganese octylate, calcium octylate, sodium octylate, and potassium octylate. One of these catalysts can be used, or two or more of these solvents can be appropriately mixed and used. Among these, amine compounds, aliphatic amines having aromatic rings, and heterocyclic compounds are preferable and triethylamine and 4-dimethylaminopyridine are more preferable from the viewpoint of good reactivity. The amount used in the case of using a catalyst is usually 0.0001 to 1000 parts by mass based on 1 part by mass of the alcohol compound.

Examples of the method for adding the catalyst include a method in which the catalyst is directly added to an alcohol compound and/or an acid anhydride, and a method in which a solution obtained by dissolving the catalyst in a soluble solvent or the like is added to an alcohol compound, an acid anhydride, and/or a solvent containing these.

When esterification is performed using a catalyst, the reaction temperature of esterification is not particularly limited depending on the amount of the catalyst and the solvent used, but is usually $-20$ to $150°$ C. The reaction time is also not particularly limited, but is usually 0.5 to 100 hours. The reaction may be completed in one stage or may be carried out in two or more stages.

In the present embodiment, the alcohol compound represented by the formula (4) and the acid anhydride represented by the formula (5) are relatively highly reactive and can be esterified in the absence of a catalyst. The acid anhydride represented by the formula (5) preferably contains an acid anhydride represented by the formula (6) because the acid anhydride has a higher reactivity with an alcohol compound. In the present embodiment, "in the absence of a catalyst" means that no catalyst contributing to the esterification reaction is added or only a trace amount is added. Specifically, it means that the catalyst is 50 ppm or less based on 1 part by mass of the alcohol compound represented by the formula (4) during the reaction. In the reaction, the catalyst contributing to the esterification reaction is preferably 0 ppm.

When esterification is performed in the absence of a catalyst, the solvent is preferably a halogen solvent, a ketone solvent, or an ester solvent from the viewpoint that the solvents can sufficiently dissolve the alcohol compound and the acid anhydride, and can also sufficiently dissolve the obtained compound (A). Further, it is more preferable to use a halogen solvent and an ester solvent from the viewpoint that superior solubility can be exhibited and hydrolysis of the acid anhydride can be suppressed. Furthermore, an ester solvent is more preferable because the alcohol compound and the acid anhydride can be favorably reacted with each other, hydrolysis of the acid anhydride can be suppressed, and environmental load can be reduced. The halogen solvent is preferably dichloromethane from the viewpoint that superior solubility can be exhibited. The ketone solvent is preferably methyl ethyl ketone from the viewpoint that superior solubility can be exhibited. The ester solvent is preferably butyl acetate, γ-butyrolactone, or propylene glycol monomethyl ether acetate from the viewpoint that superior solubility can be exhibited.

By using such a solvent in the absence of a catalyst, the step of isolating the compound (A) from the reaction mixture described later and the purification step can be omitted. The reaction temperature and reaction time are as described below.

The reason for this is not certain, but the present inventors estimate it as follows. That is, by using a halogen solvent, a ketone solvent and an ester solvent, hydrolysis of the acid anhydride represented by the formula (5) is suitably suppressed, and side reactions other than the intended esterification reaction product can be suppressed. Therefore, it is presumed that impurities are less likely to be generated and a target product having high purity can be obtained.

The amount of the solvent to be used is usually 20 to 2000 parts by mass based on 100 parts by mass of the total of the alcohol compound and the acid anhydride, and is preferably 20 to 1000 parts by mass and more preferably 20 to 500 parts by mass because the environmental load can be reduced.

When esterification is performed in the absence of a catalyst, the reaction temperature of esterification can be appropriately set depending on the solvent used, but is usually $-20$ to $150°$ C., more preferably 0 to $150°$ C., and still more preferably 20 to $120°$ C. because esterification proceeds more favorably.

When esterification is performed in the absence of a catalyst, the reaction time is usually 0.5 to 100 hours, more preferably 0.5 to 80 hours, and still more preferably 0.5 to 50 hours, because side reactions are suppressed and esterification proceeds more favorably. The reaction may be completed in one stage or may be carried out in two or more stages.

When an ester solvent is used as the solvent, the alcohol compound and the acid anhydride can be sufficiently esterified in the absence a catalyst, so that the cost required for the catalyst can be reduced, the step of removing the catalyst can be omitted, impurities are less likely to be generated and compounds having relatively high purity can be obtained. Therefore, under these production conditions, the step of isolating the compound (A) from the reaction mixture described later and the purification step can be omitted. The reaction temperature and reaction time are as described above.

The reason for this is not certain, but the present inventors estimate it as follows. That is, the ester solvent can further suppress hydrolysis of the acid anhydride represented by the formula (5), and side reactions other than the intended esterification reaction can be further suppressed. Therefore, it is presumed that impurities are less likely to be generated compared to other solvents, and a target product having higher purity can be obtained.

In the method for isolating the target compound (A) from a reaction mixture containing the compound (A), the target compound (A) can be isolated by filtration or centrifugation when the target product is precipitated from the reaction solvent. When the target product is dissolved in the reaction solvent, the target product can be isolated by distilling off the solvent under reduced pressure, adding an appropriate poor solvent to the reaction mixture, or discharging the reaction mixture into a poor solvent to precipitate the target compound, followed by filtration or centrifugation, or the like. Examples of the poor solvent include hydrocarbons such as hexane, heptane, cyclohexane, toluene, and xylene. One of these solvents can be used, or two or more of these solvents can be appropriately mixed and used.

When the isolated compound (A) needs to be further purified, it may be purified by using a known method. Examples of such methods include distillation purification methods, recrystallization methods, column chromatography methods, sludge treatment, and activated carbon treatment.

The obtained compound (A) can be identified by a known method such as NMR (nuclear magnetic resonance analysis). The purity of the compound (A) can be analyzed by, for example, GPC, liquid chromatography, IR spectroscopy and the like. Volatile components such as by-products and residual solvents in the compound (A) can be quantitatively analyzed by, for example, GPC and gas chromatography. The halogen compound remaining in the compound (A) can be identified by, for example, a liquid chromatograph mass spectrometer. The halogen compound remaining in the compound (A) can also be quantified by ion chromatography after decomposition by potentiometric titration using a silver nitrate solution or a combustion method.

[Resin Composition]

A resin composition of the present embodiment contains the compound (A), and is suitably used for the production of a multilayer printed wiring board. By using the resin composition, in an exposure step and a development step in the production of the multilayer printed wiring board, a cured product can be suitably obtained without inhibiting the photocuring reaction, and excellent alkaline developability can be imparted even after exposure.

In the resin composition, the content of the compound (A) is preferably 0.1 to 30 parts by mass, more preferably 0.5 to 15 parts by mass, and still more preferably 1 to 15 parts by mass, based on 100 parts by mass of the resin solid content in the resin composition, because superior alkaline developability can be imparted and good curability can be exhibited without inhibiting a photocuring reaction in the resin composition.

Further, when the resin composition contains a bismaleimide compound (B) described later and a maleimide compound (C) described later, the content of the compound (A) is preferably 0.1 to 30 parts by mass, more preferably 0.5 to 15 parts by mass, and still more preferably 1 to 15 parts by mass, based on 100 parts by mass of the total of the bismaleimide compound (B) described later and the maleimide compound (C) described later, because superior alkaline developability can be imparted and good curability can be exhibited without inhibiting the photocuring reaction in the resin composition.

[Bismaleimide Compound (B)]

The resin composition of the present embodiment preferably further contains a bismaleimide compound (B) (also referred to as component (B)). The bismaleimide compound (B) contains a constituent unit represented by the formula (7) and maleimide groups at both ends of the molecular chain.

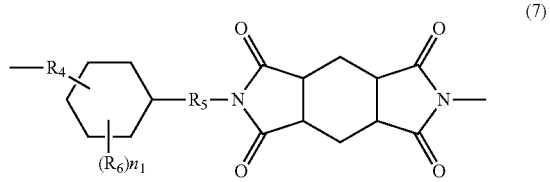

(7)

In the formula (7), $R_4$ represents a linear or branched alkylene group having 1 to 16 carbon atoms, or a linear or branched alkenylene group having 2 to 16 carbon atoms. $R_5$ represents a linear or branched alkylene group having 1 to 16 carbon atoms, or a linear or branched alkenylene group having 2 to 16 carbon atoms. Each $R_6$ independently represents a hydrogen atom, a linear or branched alkyl group having 1 to 16 carbon atoms, or a linear or branched alkenyl group having 2 to 16 carbon atoms. Each $n_1$ independently represents an integer of 1 to 10.

In addition, normally, maleimide compounds have extremely low water solubility, do not have reactivity with an alkaline component in an alkaline developing solution, and therefore hardly exhibit alkaline developability. However, since the resin composition contains the bismaleimide compound (B) together with the compound (A), the resin composition has very good alkaline developability while having excellent photocurability. The reason for this is not certain, but the present inventors estimate it as follows.

That is, the resin composition contains the compound (A) which can impart excellent alkali developability to the resin composition without inhibiting the photocuring reaction. That is, the bismaleimide compound (B) has a relatively long chain and a flexible structure, and does not have a structure which causes interaction with an alkaline component in the alkaline developing solution. Therefore, the bismaleimide compound (B) can be dissolved in the alkaline developing solution as the compound (A) is dissolved in the alkaline developing solution while the structure of the compound (A) is maintained in the alkaline developing solution. When in a development step, the alkaline developing solution flows into an unexposed portion (resin composition), the alkaline component in the alkaline developing solution and a carboxy group in the compound (A) can quickly and suitably form a salt without being hindered by the bismaleimide compound (B). Thus, water-solubility is improved. This may be the reason why the resin composition has excellent alkaline developability.

The present inventors presume that the reason why the resin composition has excellent photocuring reactivity by containing the bismaleimide compound (B) together with the compound (A) is as follows.

Normally, since maleimide compounds have poor light transmissivity, when the resin composition contains a maleimide compound, light does not sufficiently reach the photo initiator dispersed in the resin composition, and the photo initiator has difficulty generating radicals. Therefore, in general, the photo radical reaction of maleimide compounds is difficult to proceed, and even if radical polymerization or dimerization reaction of single maleimide proceeds, its reactivity is very low. However, the bismaleimide compound (B) has a constituent unit represented by the formula (7), that is, an alicyclic backbone, and therefore has very excellent light transmissivity. The compound (A) also has very excellent light transmissivity. Therefore, light reaches the photo initiator sufficiently, so that the photo radical reaction of the maleimide efficiently takes place. Using various active energy rays, the compound (A) and the bismaleimide compound (B) can be photocured together with the maleimide compound (C) described later and the photo initiator (D) described later which are optionally blended.

The bismaleimide compound (B) exhibits very excellent light transmissivity, with a transmittance of 5% or more, when a chloroform solution containing the bismaleimide compound (B) at 1% by mass is prepared and the transmittance of the chloroform solution containing the bismaleimide compound (B) at 1% by mass is measured using an active energy ray including a wavelength of 365 nm (i-line). In addition, the bismaleimide compound (B) exhibits very excellent light transmissivity, with a transmittance of 5% or more, when the transmittance of the chloroform solution containing the bismaleimide compound (B) at 1% by mass is measured using an active energy ray including a wavelength of 405 nm (h-line). Therefore, for example, upon producing a printed wiring board having a highly dense and highly detailed wiring formation (pattern) using the direct imaging method, the photo radical reaction of the maleimide occurs efficiently even when an active energy ray including a wavelength of 405 nm (h-line) is used. The transmittance at a wavelength of 365 nm (i-line) is preferably 8% or more, more preferably 10% or more, from the viewpoint of exhibiting superior light transmissivity. The transmittance at a wavelength of 405 nm (h-line) is preferably 8% or more, more preferably 10% or more, from the viewpoint of producing a printed wiring board having a more highly dense and highly detailed wiring formation (pattern). The upper limit of each of the transmittance at a wavelength of 365 nm (i-line) and the transmittance at a wavelength of 405 nm (h-line) is, for example, 99.9% or less.

Normally, the absorbance of the photo initiator tends to decrease with respect to light in a long wavelength region. For example, when an active energy ray (ray of light) including a wavelength of 405 nm (h-line) is used, a usual photo initiator does not absorb the ray because light having such a wavelength has a relatively long wavelength, and polymerization proceeds only when a photo initiator capable of suitably absorbing the light to generate radicals is used. Therefore, as the later-described photo initiator (D), a photo initiator is preferably used which exhibits very excellent absorption of light with a wavelength of 405 nm (h-line), with an absorbance of 0.1 or more, when the absorbance of a chloroform solution containing the photo initiator (D) at 0.01% by mass is measured.

Since the bismaleimide compound (B) has excellent light transmissivity as mentioned above, light reaches the photo initiator sufficiently, for example, even when an active energy ray including a wavelength of 365 nm or an active energy ray including a wavelength of 405 nm is used, radical reaction using radicals generated from the photo initiator proceeds, and even a composition containing a large amount of the bismaleimide compound (B) can be photocured.

The resin composition is excellent in alkaline developability and photocurability. The obtained cured product is excellent in heat resistance, insulation reliability and thermal stability. Therefore, according to the present embodiment, it is possible to suitably form a protective film and an insulation layer in the multilayer printed wiring board and the semiconductor device.

The mass average molecular weight of the bismaleimide compound (B) is not particularly limited as long as the effects of the present invention are exhibited, but is preferably 100 to 5000, and more preferably 300 to 4500 because a suitable viscosity can be obtained and an increase in viscosity of varnish can be suppressed. In the present embodiment, the term "mass average molecular weight" means a mass average molecular weight in terms of polystyrene standard by a gel permeation chromatography (GPC) method.

The structure of the bismaleimide compound (B) will now be described.

In the formula (7) of the bismaleimide compound (B), $R_4$ represents a linear or branched alkylene group having 1 to 16 carbon atoms, or a linear or branched alkenylene group having 2 to 16 carbon atoms. $R_4$ is preferably a linear or branched alkylene group, and more preferably a linear alkylene group because a suitable viscosity can be obtained and an increase in viscosity of varnish can be controlled.

The number of carbon atoms in the alkylene group is preferably 2 to 14, and more preferably 4 to 12 because a more suitable viscosity can be obtained and an increase in viscosity of varnish can be more reliably controlled.

Examples of the linear or branched alkylene group include a methylene group, an ethylene group, a propylene group, a 2,2-dimethylpropylene group, a butylene group, a pentylene group, a hexylene group, a heptylene group, an octylene group, a nonylene group, a decylene group, a dodecylene group, an undecylene group, a tridecylene group, a tetradecylene group, a pentadecylene group, a hexadecylene group, a neopentylene group, a dimethylbutylene group, a methylhexylene group, an ethylhexylene group, a dimethylhexylene group, a trimethylhexylene group, a methylheptylene group, a dimethylheptylene group, a trimethylheptylene group, a tetramethylheptylene group, an ethylheptylene group, a methyloctylene group, a methylnonylene group, a methyldecylene group, a methyldodecylene group, a methylundecylene group, a methyltridecylene group, a methyltetradecylene group and a methylpentadecylene group.

The number of carbon atoms in the alkenylene group is preferably 2 to 14, and more preferably 4 to 12 because a more suitable viscosity can be obtained and an increase in viscosity of varnish can be more reliably controlled.

Examples of the linear or branched alkenylene group include a vinylene group, a 1-methylvinylene group, an arylene group, a propenylene group, an isopropenylene group, a 1-butenylene group, a 2-butenylene group, a 1-pentenylene group, a 2-pentenylene group, an isopentenylene group, a cyclopentenylene group, a cyclohexenylene group and a dicyclopentadienylene group.

In the formula (1), $R_5$ represents a linear or branched alkylene group having 1 to 16 carbon atoms, or a linear or branched alkenylene group having 2 to 16 carbon atoms. $R_5$ is preferably a linear or branched alkylene group, and more preferably a linear alkylene group because a suitable viscosity can be obtained and an increase in viscosity of varnish can be controlled.

The number of carbon atoms in the alkylene group is preferably 2 to 14, and more preferably 4 to 12 because a more suitable viscosity can be obtained and an increase in viscosity of varnish can be more reliably controlled.

For the linear or branched alkylene group, $R_4$ can be referred to.

The number of carbon atoms in the alkenylene group is preferably 2 to 14, and more preferably 4 to 12 because a more suitable viscosity can be obtained and an increase in viscosity of varnish can be more reliably controlled.

For the linear or branched alkenylene group, $R_4$ can be referred to.

In the formula (7), $R_4$ and $R_5$ may be the same or different, and are preferably the same because the bismaleimide compound (B) can be more easily synthesized.

In the formula (7), each $R_6$ independently represents a hydrogen atom, a linear or branched alkyl group having 1 to 16 carbon atoms, or a linear or branched alkenyl group having 2 to 16 carbon atoms. It is preferable that each $R_6$ be independently a hydrogen atom or a linear or branched alkyl group having 1 to 16 carbon atoms because a suitable viscosity can be obtained and an increase in viscosity of varnish can be controlled, it is more preferable that one to five groups ($R_6$s) among $R_6$s be linear or branched alkyl groups each having 1 to 16 carbon atoms, and other groups ($R_6$) be hydrogen atoms, and it is still more preferable that one to three groups ($R_6$s) among $R_6$s be linear or branched alkyl groups each having 1 to 16 carbon atoms, and other groups ($R_6$) be hydrogen atoms.

The number of carbon atoms in the alkyl group is preferably 2 to 14, and more preferably 4 to 12 because a more suitable viscosity can be obtained and an increase in viscosity of varnish can be more reliably controlled.

Examples of the linear or branched alkyl group include a methyl group, an ethyl group, a n-propyl group, an isopropyl group, a 1-ethylpropyl group, a n-butyl group, a 2-butyl group, an isobutyl group, a tert-butyl group, a n-pentyl group, a 2-pentyl group, a tert-pentyl group, a 2-methylbutyl group, a 3-methylbutyl group, a 2,2-dimethylpropyl group, a n-hexyl group, a 2-hexyl group, a 3-hexyl group, a n-heptyl group, a n-octyl group, a 2-methylpentyl group, a 3-methylpentyl group, a 4-methylpentyl group, a 2-methylpentan-3-yl group and a n-nonyl group.

The number of carbon atoms in the alkenyl group is preferably 2 to 14, and more preferably 4 to 12 because a more suitable viscosity can be obtained and an increase in viscosity of varnish can be more reliably controlled.

Examples of the linear or branched alkenyl group include a vinyl group, an allyl group, a 4-pentenyl group, an isopropenyl group, an isopentenyl group, a 2-heptenyl group, a 2-octenyl group and a 2-nonenyl group.

In the formula (7), each $n_1$ independently represents an integer of 1 to 10.

The maleimide group is represented by the formula (18), and the N atom is bonded to the molecular chain of the bismaleimide compound (B). In addition, the maleimide groups bonded to the bismaleimide compound (B) may be all the same or different, and the maleimide groups at both ends of the molecular chain are preferably the same.

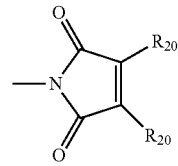

(18)

In the formula (18), each $R_{20}$ independently represents a hydrogen atom, or a linear or branched alkyl group having 1 to 4 carbon atoms. Each $R_{20}$ is preferably a hydrogen atom because photocuring is suitably performed.

The number of carbon atoms in the alkyl group is preferably 1 to 3, and more preferably 1 or 2 because photocuring is suitably performed.

For the linear or branched alkyl group, $R_6$ can be referred to.

Examples of such a bismaleimide compound (B) include a maleimide compound represented by the formula (19). One of these bismaleimide compounds can be used, or two or more thereof can be appropriately mixed and used.

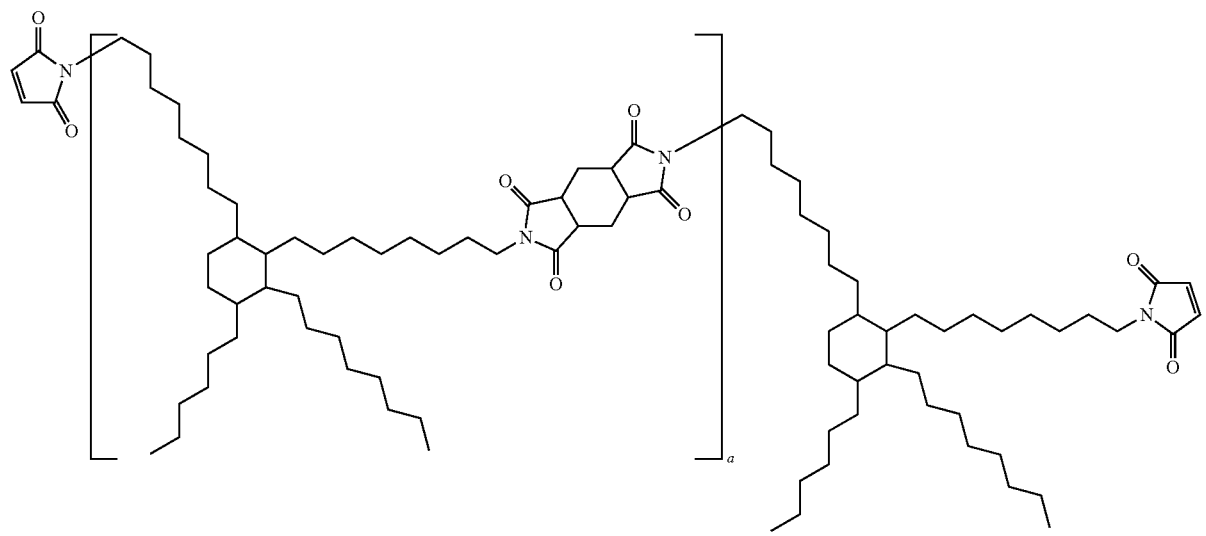

(19)

The bismaleimide compound (B) has maleimide groups at both ends of the molecular chain. The term "both ends" means both ends of the molecular chain of the bismaleimide compound (B), and for example, when the structural unit represented by the formula (7) is present at an end of the molecular chain of the bismaleimide compound (B), the maleimide group is present at an end of the molecular chain of $R_4$, at an end of the molecular chain on the N atom of the maleimide ring, or at each of both the ends. The bismaleimide compound (B) may have maleimide groups at positions other than both ends of the molecular chain.

In the formula (19), a represents an integer of 1 to 10. a is preferably an integer of 1 to 6 because a more suitable viscosity can be obtained and an increase in viscosity of varnish can be more reliably controlled.

As the bismaleimide compound (B), commercial products can also be used. Examples of the commercial products include MIZ-001 manufactured by Nippon Kayaku Co., Ltd. (trade name, containing the maleimide compound of the formula (19)).

In the resin composition, the content of the bismaleimide compound (B) is preferably 10 to 90 parts by mass, more preferably 30 to 80 parts by mass, and still more preferably 40 to 70 parts by mass based on 100 parts by mass of the resin solid content, from the viewpoint that a cured product containing the bismaleimide compound as a main component can be obtained, photocurability can be improved, and superior heat resistance and thermal stability can be obtained.

Further, when the resin composition contains the bismaleimide compound (B) and the maleimide compound (C) described later, the content of the bismaleimide compound (B) is preferably 10 to 90 parts by mass, more preferably 30 to 80 parts by mass, and still more preferably 40 to 70 parts by mass based on 100 parts by mass of the total of the bismaleimide compound (B) and the maleimide compound (C) described later, from the viewpoint that a cured product containing the bismaleimide compound as a main component can be obtained, photocurability can be improved, and superior heat resistance and thermal stability can be obtained.

One of these bismaleimide compounds (B) can be used, or two or more thereof can be appropriately mixed and used.

(Method for producing bismaleimide compound (B)) The bismaleimide compound (B) can be produced by a known method. For example, 1,2,4,5-cyclohexanetetracarboxylic acid dianhydride, a monomer containing a diamine containing dimer diamine or the like, and maleic anhydride are subjected to a polyaddition reaction at a temperature of usually about 80 to 250° C., preferably about 100 to 200° C. for usually about 0.5 to 50 hours, preferably about 1 to 20 hours to obtain a polyadduct. Thereafter, the polyadduct is subjected to an imidization reaction, that is, a dehydration ring-closure reaction, at a temperature of generally about 60 to 120° C., preferably about 80 to 100° C., for generally about 0.1 to 2 hours, preferably about 0.1 to 0.5 hours, thereby obtaining the bismaleimide compound (B).

The dimer diamine can be obtained by, for example, a reductive amination reaction of a dimer acid, and the amination reaction can be conducted by, for example, a known method such as a reduction method using ammonia and a catalyst (e.g. the method described in Japanese Patent Laid-Open No. 9-12712). The dimer acid is a dibasic acid obtained by dimerization of an unsaturated fatty acid through an intermolecular polymerization reaction or the like. Depending on synthesis conditions and purification conditions, a small amount of monomer acids and trimer acids are normally contained in addition to the dimer acid. After the reaction, double bonds remain in the obtained molecule, and in the present embodiment, the dimer acids also include those formed into saturated dibasic acids by reduction of double bonds present in the molecule through a hydrogenation reaction. The dimer acid can be obtained by, for example, polymerizing an unsaturated fatty acid using Lewis acid and Broensted acid as catalysts. The dimer acid can be produced by a known method (e.g. the method described in Japanese Patent Laid-Open No. 9-12712). Examples of the unsaturated fatty acid include crotonic acid, myristoleic acid, palmitoleic acid, oleic acid, elaidic acid, vaccenic acid, gadoleic acid, eicosenoic acid, erucic acid, nervonic acid, linoleic acid, pinolenic acid, eleostearic acid, mead acid, dihomo-γ-linolenic acid, eicosatrienoic acid, stearidonic acid, arachidonic acid, eicosatetraenoic acid, adrenic acid, bosseopentaenoic acid, Osbond acid, clupanodonic acid, tetracosapentaenoic acid, docosahexaenoic acid and Nisinic acid. The number of carbon atoms in the unsaturated fatty acid is typically 4 to 24, and preferably 14 to 20.

In production of the bismaleimide compound (B), it is preferable that the monomer containing a diamine be dissolved or dispersed in a slurry form in an organic solvent in an inert atmosphere of, for example, argon, nitrogen or the like to form a monomer solution containing a diamine in advance. It is preferable that the 1,2,4,5-cyclohexanetetracarboxylic dianhydride be added to the monomer solution containing a diamine after being dissolved or dispersed in a slurry form in an organic solvent, or in a solid state.

A desired bismaleimide compound (B) can be obtained by adjusting the number of moles of the 1,2,4,5-cyclohexanetetracarboxylic dianhydride and the number of moles of the total amount of the monomer containing a diamine and the maleimide compound.

Various known solvents can be used for the polyaddition reaction and the imidization reaction. Examples of the solvent include amides such as N,N-dimethylformamide, N,N-dimethylacetamide and N-methyl-2-pyrrolidone; ketones such as acetone, methyl ethyl ketone, methyl isobutyl ketone, cyclohexanone and isophorone; esters such as γ-butyrolactone, γ-valerolactone, δ-valerolactone, γ-caprolactone, ε-caprolactone, α-methyl-γ-butyrolactone, ethyl lactate, methyl acetate, ethyl acetate and butyl acetate; aliphatic alcohols having 1 to 10 carbon atoms such as methanol, ethanol and propanol; aromatic group-containing phenols such as phenol and cresol; aromatic group-containing alcohols such as benzyl alcohol; glycols such as ethylene glycol and propylene glycol, monoethers or diethers of these glycols and methanol, ethanol, butanol, hexanol, octanol, benzyl alcohol, phenol, cresol and the like, or glycol ethers such as esters of these monoethers; cyclic ethers such as dioxane and tetrahydrofuran; cyclic carbonates such as ethylene carbonate and propylene carbonate; aliphatic hydrocarbons and aromatic hydrocarbons such as toluene and xylene; and aprotic polar solvents such as dimethylsulfoxide. One of these solvents can be used, or two or more thereof can be combined and used as necessary.

It is preferable to use a catalyst in the imidization reaction. As the catalyst, for example, tertiary amines and dehydration catalysts can be used. The tertiary amine is preferably a heterocyclic tertiary amine, and examples thereof include pyridine, picoline, quinoline and isoquinoline. Examples of the dehydration catalyst include acetic anhydride, propionic anhydride, n-butyric anhydride, benzoic anhydride and trifluoroacetic anhydride.

For the amount of the catalyst added, it is preferable that for example, the amount of an imidizing agent be 0.5 to 5.0 times the amount of amide groups on a molar basis, and the amount of the dehydration catalyst be 0.5 to 10.0 times the amount of amide groups on a molar basis.

After completion of the imidization reaction, the solution may be used as a bismaleimide compound (B) solution, or a poor solvent may be added to the reaction solvent to form the bismaleimide compound (B) into a solid matter. Examples of the poor solvent include water, methyl alcohol, ethyl alcohol, 2-propyl alcohol, ethylene glycol, triethylene glycol, 2-butyl alcohol, 2-pentyl alcohol, 2-hexyl alcohol, cyclopentyl alcohol, cyclohexyl alcohol, phenol and t-butyl alcohol.

<Maleimide Compound (C)>

The resin composition of the present embodiment preferably further contains a maleimide compound (C) (also referred to as component (C)) other than the bismaleimide compound (B) according to the present embodiment. The maleimide compound (C) is at least one selected from the group consisting of a compound represented by the formula (8), a compound represented by the formula (9), a compound represented by the formula (10), a compound represented by the formula (11), a compound represented by the formula (12), and a compound represented by the formula (13). One of these maleimide compounds (C) can be used alone, or two or more of these maleimide compounds (C) can be appropriately mixed and used. The maleimide compound (C) is preferably a compound represented by the formula (8), a compound represented by the formula (9), or a compound represented by the formula (10), and more preferably a compound represented by the formula (8) or a compound represented by the formula (9), from the viewpoint of exhibiting superior heat resistance and thermal stability, and good solubility in a solvent, low melting point, low water absorption, and good compatibility with other resins.

As described above, the photoradical reactivity of the maleimide compound is usually very low. However, the bismaleimide compound (B) is very excellent in light transmissivity as described above. In addition, since the compound (A) also has very excellent light transmissivity, by using the bismaleimide compound (A) together with the compound (A) and the maleimide compound (C), and a photo initiator (D) described later which is blended as necessary, light reaches the photo initiator sufficiently, the photo radical reaction of the maleimide efficiently takes place, and photocuring can be performed using various active energy rays.

Since the compound (A) and the bismaleimide compound (B) have excellent light transmissivity, light reaches the photo initiator sufficiently, for example, even when an active energy ray including a wavelength of 365 nm or an active energy ray including a wavelength of 405 nm is used, radical reaction using radicals generated from the photo initiator proceeds, and even a composition containing the maleimide compound (C) can be photocured.

The resin composition is excellent in alkaline developability and photocurability. Further, the obtained cured product has excellent heat resistance, insulation reliability and thermal stability, a protective film and an insulation layer can be suitably formed.

Next, the compounds represented by the formulas (8) to (13) contained in the maleimide compound (C) will be described.

(Compound Represented by Formula (8))

The compound represented by the formula (8) is the following compound.

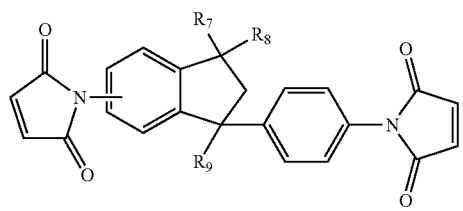

(8)

In the formula (8), $R_7$, $R_8$, and $R_9$ each independently represent a hydrogen atom, or a linear or branched alkyl group having 1 to 8 carbon atoms and optionally having a substituent.

Examples of the linear or branched alkyl group having 1 to 8 carbon atoms and optionally having a substituent include a methyl group, an ethyl group, a propyl group, an isopropyl group, a n-butyl group, an isobutyl group, a tert-butyl group, a n-pentyl group, a 1-ethylpropyl group, a 2,2-dimethylpropyl group, a cyclopentyl group, a hexyl group, and a heptyl group. A hydrogen atom in these alkyl groups may be substituted with a halogen atom such as a fluorine atom or a chlorine atom, a cyano group, or the like. Among these alkyl groups, a methyl group, an ethyl group, an isopropyl group, and a tert-butyl group are preferable, a methyl group, an ethyl group, and an isopropyl group are more preferable, and a methyl group is still more preferable from the viewpoint of exhibiting superior photocurability, heat resistance, and thermal stability, and good solubility in a solvent, low melting point, low water absorption, and good compatibility with other resins.

The compound represented by the formula (8) is more preferably a compound represented by the formula (20) (also referred to as TMDM in the present embodiment) from the viewpoint of exhibiting superior photocurability, heat resistance, and thermal stability, solubility in a solvent, low melting point, low water absorption, and compatibility with other resins.

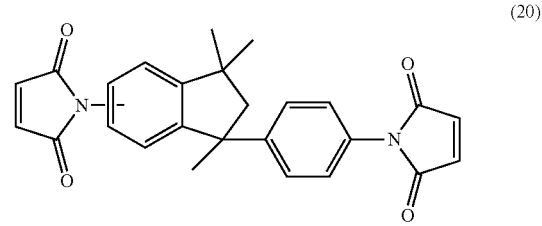

(20)

(Compound Represented by Formula (9))

The compound represented by the formula (9) is the following compound.

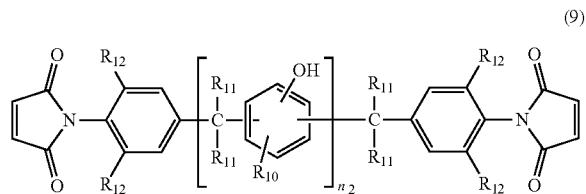

(9)

In the formula (9), $R_{10}$, $R_{11}$, and $R_{12}$ each independently represent a hydrogen atom, a hydroxyl group, or a linear or branched alkyl group having 1 to 6 carbon atoms and optionally having a substituent. $n_2$ is an integer of 1 to 10.

As the linear or branched alkyl group having 1 to 6 carbon atoms, $R_2$ in the formula (1) can be referred to. The alkyl group is preferably a methyl group, an ethyl group, an n-propyl group, or an isopropyl group, and more preferably a methyl group, from the viewpoint of exhibiting good solubility in a solvent, low melting point, low water absorption, and good compatibility with other resins.

Further, in $R_{10}$, $R_{11}$, and $R_{12}$, it is preferable that $R_{10}$ and $R_{12}$ be linear or branched alkyl groups having 1 to 6 carbon atoms and $R_{11}$ be a hydrogen atom from the viewpoint of exhibiting superior solubility in a solvent. Preferred alkyl groups are as described above.

$n_2$ is preferably an integer of 1 to 10, and more preferably an integer of 1 to 6, from the viewpoint that the solubility in a solvent is excellent, a more suitable viscosity is obtained, and an increase in the viscosity of the varnish can be more reliably controlled.

As the compound represented by the formula (9), a commercially available product may be used, and examples thereof include BCPH13 (trade name) represented by the formula (21) manufactured by Gun Ei Chemical Industry Co., Ltd., BCPH01 (trade name) manufactured by Gun Ei Chemical Industry Co., Ltd., and BMCX426 (trade name) represented by the formula (22) manufactured by Gun Ei Chemical Industry Co., Ltd.

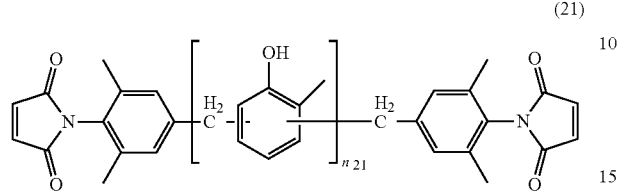

(21)

In the formula (21), $n_{21}$ is an integer of 1 to 5.

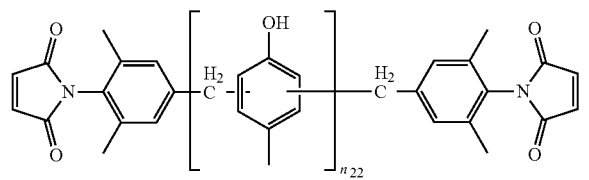

(22)

In the formula (22), $n_{22}$ is an integer of 1 to 10.

(Compound Represented by Formula (10))

The compound represented by the formula (10) is the following compound.

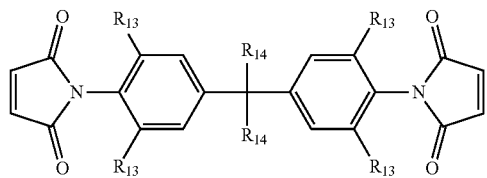

(10)

In the formula (10), each $R_{13}$ independently represents a hydrogen atom, a methyl group, or an ethyl group, and each $R_{14}$ independently represents a hydrogen atom or a methyl group.

$R_{13}$ is preferably a methyl group or an ethyl group from the viewpoint of exhibiting good solubility in solvents, a low melting point, a low water absorption property, and good compatibility with other resins.

$R_{14}$ is preferably a hydrogen atom from the viewpoint of exhibiting good solubility in solvents, a low melting point, a low water absorption property, and good compatibility with other resins.

As the maleimide compound represented by the formula (10), commercial products may also be used, and examples thereof include BMI-70 (trade name) represented by the formula (23) manufactured by K•I Chemical Industry Co., LTD.

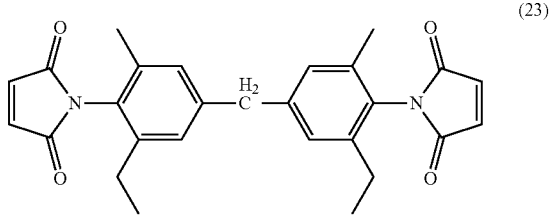 [SMILES: CCc1cc(Cc2cc(C)c(N3C(=O)C=CC3=O)c(CC)c2)cc(C)c1N1C(=O)C=CC1=O]

(23)

(Compound Represented by Formula (11))

The compound represented by the formula (11) is the following compound.

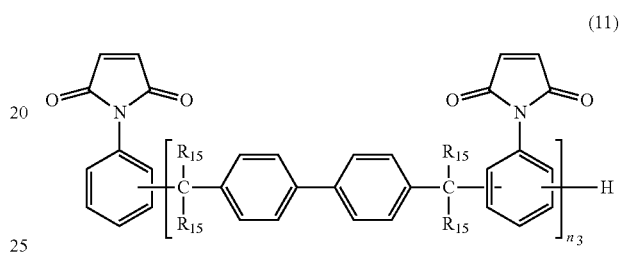

(11)

In the formula (11), each $R_{15}$ independently represents a hydrogen atom or a methyl group. $n_3$ represents an integer of 1 to 10.

As the maleimide compound represented by the formula (11), commercial products may also be used, and examples thereof include MIR-3000 (trade name) represented by the formula (24) manufactured by Nippon Kayaku Co., Ltd.

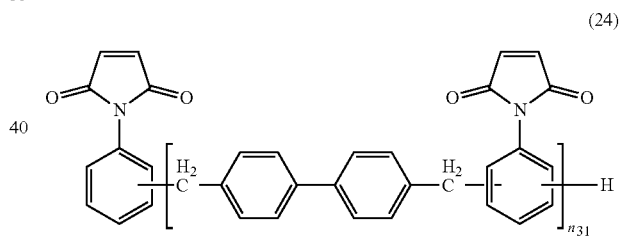

(24)

In the formula (24), $n_{31}$ is an integer of 1 to 10.

(Compound Represented by Formula (12))

The compound represented by the formula (12) is the following compound.

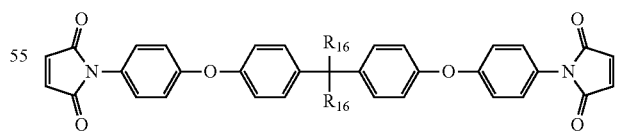

(12)

In the formula (12), each $R_{16}$ independently represents a hydrogen atom, a methyl group or an ethyl group.

$R_{16}$ is preferably a methyl group or an ethyl group from the viewpoint of exhibiting good solubility in solvents, a low melting point, a low water absorption property, and good compatibility with other resins.

As the maleimide compound represented by the formula (12), commercial products may also be used, and examples thereof include BMI-80 (trade name) represented by the formula (25) manufactured by K•I Chemical Industry Co., LTD.

(25)

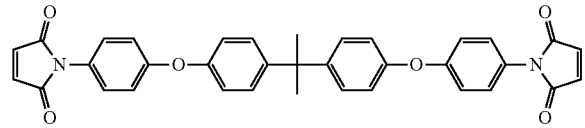

(Compound Represented by Formula (13))

The compound represented by the formula (13) is the following compound.

(13)

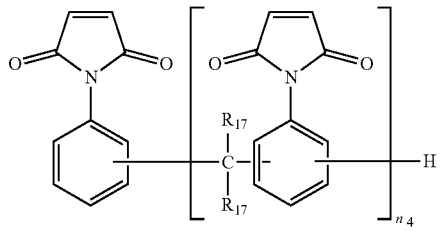

In the formula (13), each $R_{17}$ independently represents a hydrogen atom or a methyl group. $n_4$ represents an integer of 1 to 10.

$R_{17}$ is preferably a hydrogen atom from the viewpoint of exhibiting good solubility in solvents, a low melting point, a low water absorption property, and good compatibility with other resins.

$n_4$ is more preferably an integer of 1 to 5, from the viewpoint that the solubility in a solvent is excellent, a more suitable viscosity is obtained, and an increase in the viscosity of the varnish can be more reliably controlled.

As the maleimide compound represented by the formula (13), commercial products may also be used, and examples thereof include BMI-2300 (trade name) represented by the formula (26) manufactured by Daiwakasei Industry Co., LTD.

(26)

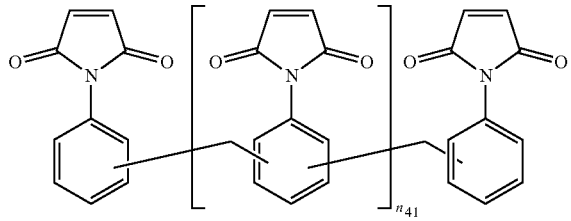

In the formula (26), $n_{41}$ is an integer of 1 to 5.

In the resin composition, the content of the maleimide compound (C) is preferably 10 to 90 parts by mass, more preferably 20 to 70 parts by mass, and still more preferably 30 to 60 parts by mass based on 100 parts by mass of the resin solid content, from the viewpoint that superior heat resistance and thermal stability can be obtained.

Further, when the resin composition contains the bismaleimide compound (B) and the maleimide compound (C), the content of the maleimide compound (C) is preferably 10 to 90 parts by mass, more preferably 20 to 70 parts by mass, and still more preferably 30 to 60 parts by mass based on 100 parts by mass of the total of the bismaleimide compound (B) and the maleimide compound (C), from the viewpoint that superior heat resistance and thermal stability can be obtained.

[Photo Initiator (D)]

The resin composition of the present embodiment preferably further contains a photo initiator (D) (also referred to as component (D)). The photo initiator (D) is not particularly limited, and photo initiators can be used which are publicly known in fields where photo initiators are generally used for photocurable resin compositions. The photo initiator (D) is used together with the compound (A) and the bismaleimide compound (B), the maleimide compound (C), and the like, which are optionally blended, for photocuring by using various active energy rays.

Examples of the photo initiator (D) include radical type photo initiators such as benzoins such as benzoin, benzoin methyl ether, benzoin ethyl ether, benzoin isopropyl ether and benzoin isobutyl ether; organic peroxides exemplified by benzoyl peroxide, lauroyl peroxide, acetyl peroxide, parachlorobenzoyl peroxide, di-tert-butyl-di-perphthalate and the like; phosphine oxides such as 2,4,6-trimethylbenzoyl-diphenyl-phosphine oxide, bis(2,4,6-trimethylbenzoyl)-phenylphosphine oxide, benzoyl-diphenyl-phosphine oxide and bisbenzoyl-phenyphosphine oxide; acetophenones such as acetophenone, 2,2-diethoxy-2-phenylacetophenone, 1,1-dichloroacetophenone, 2-hydroxy-2-methylphenylpropan-1-one, diethoxyacetophenone, 1-hydroxycyclohexylphenylketone, 2-methyl-1-[4-(methylthio)phenyl]-2-morpholino-propan-1-one and 2-benzyl-2-dimethylamino-1-(4-morpholinophenyl)-butanone-1; anthraquinones such as 2-ethylanthraquinone, 2-t-butylanthraquinone, 2-chloroanthraquinone and 2-amylanthraquinone; thioxanthones such as 2,4-diethylthioxanthone, 2-isopropylthioxanthone and 2-chlorothioxanthone; ketals such as acetophenone dimethyl ketal and benzyl dimethyl ketal; benzophenones such as benzophenone, 4-benzoyl-4'-methyldiphenyl sulfide and 4,4'-bismethylaminobenzophenone; and oxime esters such as 1,2-octanedione, 1-[4-(phenylthio)-,2-(O-benzoyloxime)] and ethanone, 1-[9-ethyl-6-(2-methylbenzoyl)-9H-carbazol-3-yl]-,1-(0-acetyloxime);

diazonium salts of Lewis acid such as p-methoxyphenyldiazonium fluorophosphonate and N,N-diethylaminophenyldiazonium hexafluorophosphonate; iodonium salts of Lewis acid such as diphenyliodonium hexafluorophosphonate and diphenyliodonium hexafluoroantimonate; sulfonium salts of Lewis acid such as triphenylsulfonium hexafluorophosphonate and triphenylsulfonium hexafluoroantimonate; phosphonium salts of Lewis acid such as triphenylphosphonium hexafluoroantimonate; additional halides; triazine-based initiators; borate-based initiators; and cationic photo initiators such as additional photoacid generators.

As the photo initiator (D), commercially available products may be used, and examples thereof include Omnirad® 369 (trade name) manufactured by IGM Resins B.V., Omnirad® 819 (trade name) manufactured by IGM Resins B.V., Omnirad® 819DW (trade name) manufactured by IGM Resins B.V., Omnirad® 907 (trade name) manufactured by IGM Resins B.V., Omnirad® TPO (trade name) manufactured by IGM Resins B.V., Omnirad® TPO-G (trade name) manufactured by IGM Resins B.V., Omnirad® 784 (trade name) manufactured by IGM Resins B.V., Irgacure® OXE01 (trade name) manufactured by BASF Japan Ltd., Irgacure® OXE02 (trade name) manufactured by BASF Japan Ltd., Irgacure® OXE03 (trade name) manufactured by BASF Japan Ltd., and Irgacure® OXE04 (trade name) manufactured by BASF Japan Ltd.

One of these photo initiators (D) can be used, or two or more thereof can be appropriately mixed and used.

The photo initiator (D) has an absorbance of preferably 0.1 or more when a chloroform solution containing the photo initiator (D) at 0.01% by mass is prepared, and the absorbance of the chloroform solution containing the photo initiator (D) at 0.01% by mass is measured using an active energy ray including a wavelength of 365 nm (i-line). In this case, the photo initiator (D) exhibits very excellent light absorption. In addition, the photo initiator (D) has an absorbance of preferably 0.1 or more when the absorbance of a chloroform solution containing the photo initiator (D) at 0.01% by mass is measured using an active energy ray including a wavelength of 405 nm (h-line). Even in this case, very excellent light absorption is exhibited. When such a photo initiator (D) is used, for example, upon producing a printed wiring board having a highly dense and highly detailed wiring formation (pattern) using the direct imaging method, the photo radical reaction of the maleimide occurs efficiently even when an active energy ray including a wavelength of 405 nm (h-line) is used. The absorbance at a wavelength of 365 nm (i-line) is more preferably 0.15 or more because a resin composition that is superior in photocurability can be obtained. The absorbance at a wavelength of 405 nm (h-line) is more preferably 0.15 or more because a resin composition that is superior in photocurability can be obtained. The upper limit of each of the absorbance at a wavelength of 365 nm (i-line) and the absorbance at a wavelength of 405 nm (h-line) is, for example, 99.9 or less.

As such a photo initiator (D), a compound represented by the formula (14) is preferable.

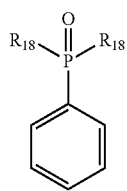

(14)

In the formula (14), each $R_{18}$ independently represents a substituent represented by the formula (15) or a phenyl group.

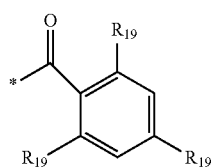

(15)

In the formula (15), each $R_{19}$ independently represents a hydrogen atom or a methyl group. In the formula (15), -* represents a bonding hand with a phosphorus atom (P) directly bonded to $R_{18}$ in the formula (14).

As for the compound represented by the formula (14), when a chloroform solution containing this compound at 0.01% by mass is prepared and the absorbance of this chloroform solution is measured using an active energy ray including a wavelength of 365 nm (i-line), the absorbance is 0.1 or more, exhibiting very excellent absorption of the light with a wavelength of 365 nm (i-line). Therefore, this compound suitably generates radicals in response to the light with a wavelength of 365 nm (i-line). The absorbance is preferably 0.15 or more. The upper limit value is, for example, 10.0 or less, and may be 5.0 or less, or 2.0 or less.

As for the compound represented by the formula (14), when a chloroform solution containing this compound at 0.01% by mass is prepared and the absorbance of this chloroform solution is measured using an active energy ray including a wavelength of 405 nm (h-line), the absorbance is 0.1 or more, exhibiting very excellent absorption of the light with a wavelength of 405 nm (h-line). Therefore, this compound suitably generates radicals in response to the light with a wavelength of 405 nm (h-line). The absorbance is more preferably 0.15 or more. The upper limit value is, for example, 10.0 or less, and may be 5.0 or less, or 2.0 or less.

In the formula (14), each $R_{18}$ independently represents a substituent represented by the formula (15) or a phenyl group. It is preferable that one or more among $R_{18}$s be the substituents represented by the formula (15).

In the formula (15), each $R_{19}$ independently represents a hydrogen atom or a methyl group. It is preferable that one or more among $R_{19}$s be methyl groups, and it is more preferable that all should be methyl groups.

Examples of the compound represented by the formula (14) include acylphosphine oxides such as 2,4,6-trimethyl-benzoyl-diphenyl-phosphine oxide and bis(2,4,6-trimethyl-benzoyl)-phenylphosphine oxide. Of these, bis(2,4,6-trimethylbenzoyl)-phenylphosphine oxide is preferable because it has excellent light transmissivity. One of these compounds can be used, or two or more thereof can be appropriately mixed and used.

Acylphosphine oxides exhibit very excellent absorption of an active energy ray including a wavelength of 405 nm (h-line) and can suitably radical polymerize the bismaleimide compound (B) and the maleimide compound (C) at a wavelength of 405 nm (h-line). Therefore, according to the present embodiment, it is possible to suitably produce a resin composition which does not hinder photocuring reaction and has excellent photocurability in an exposure step and is capable of imparting excellent alkaline developability in a development step particularly when used for a multilayer printed wiring board; and a resin sheet, a multilayer printed wiring board and a semiconductor device obtained using the resin composition.

In the resin composition, the content of the photo initiator (D) is preferably 0.1 to 50 parts by mass, more preferably 0.2 to 30 parts by mass, and still more preferably 0.3 to 10 parts by mass, based on 100 parts by mass of the resin solid content, from the viewpoint that photocuring sufficiently proceeds without inhibiting the photocuring reaction in the resin composition and the exposed portion is sufficiently insolubilized in alkaline developability.

Further, when the resin composition contains the bismaleimide compound (B) and the maleimide compound (C), the content of the photo initiator (D) is preferably 0.1 to 50 parts by mass, more preferably 0.2 to 30 parts by mass, and still more preferably 0.3 to 10 parts by mass based on 100 parts by mass of the total of the bismaleimide compound (B) and the maleimide compound (C) from the viewpoint that photocuring sufficiently proceeds without inhibiting the photocuring reaction in the resin composition and the exposed portion is sufficiently insolubilized in alkaline developability.

[Maleimide Compound (E) Other than Bismaleimide Compound (B) and Maleimide Compound (C)]

In the resin composition of the present embodiment, a maleimide compound (E) (also referred to as component (E)) other than the bismaleimide compound (B) and the maleimide compound (C) can be used as long as the effects of the present invention are exhibited. The compound (A) and the bismaleimide compound (B) have very excellent light transmissivity as described above, so that even when the maleimide compound (E) is used, light reaches the photo initiator sufficiently, the photo radical reaction of the maleimide efficiently takes place, and photocuring can be performed using various active energy rays. Therefore, light reaches the photo initiator sufficiently, for example, even when an active energy ray including a wavelength of 365 nm or an active energy ray including a wavelength of 405 nm is used, radical reaction using radicals generated from the photo initiator proceeds, and even a composition containing the maleimide compound (E) can be photocured.

The maleimide compound (E) is not particularly limited as long as it is a compound other than the bismaleimide compound (B) and the maleimide compound (C) and has one or more maleimide groups in the molecule. Specific examples thereof include N-phenylmaleimide, N-cyclohexylmaleimide, N-hydroxyphenylmaleimide, N-anilinophenylmaleimide, N-carboxyphenylmaleimide, N-(4-carboxy-3-hydroxyphenyl)maleimide, 6-maleimidohexanoic acid, 4-maleimidobutyric acid, bis(4-maleimidophenyl)methane, 2,2-bis{4-(4-maleimidophenoxy)-phenyl}propane, 4,4-diphenylmethanebismaleimide, bis(3,5-dimethyl-4-maleimidophenyl)methane, bis(3-ethyl-5-methyl-4-maleimidophenyl)methane, bis(3,5-diethyl-4-maleimidophenyl)methane, phenylmethanemaleimide, 0-phenylenebismaleimide, m-phenylenebismaleimide, p-phenylenebismaleimide, o-phenylenebiscitraconimide, m-phenylenebiscitraconimide, p-phenylenebiscitraconimide, 2,2-bis(4-(4-maleimidophenoxy)-phenyl)propane, 3,3-dimethyl-5,5-diethyl-4,4-diphenylmethanebismaleimide, 4-methyl-1,3-phenylene-bismaleimide, 1,2-bis(maleimido)ethane, 1,4-bis(maleimido)butane, 1,5-bis(maleimido)pentane, 1,5-bismalleimide-2-methylpentane, 1,6-bis(maleimido)hexane, 1,6-bismaleimido-(2,2,4-trimethyl)hexane, 1,8-bismaleimido-3,6-dioxaoctane, 1,11-bismaleimido-3,6,9-trioxaundecane, 1,3-bis(maleimidomethyl)cyclohexane, 1,4-bis(maleimidomethyl)cyclohexane, 4,4-diphenyl ether bismaleimide, 4,4-diphenyl sulfone bismaleimide, 1,3-bis(3-maleimidophenoxy)benzene, 1,3-bis(4-maleimidophenoxy)benzene, 4,4-diphenylmethanebiscitraconimide, 2,2-bis[4-(4-citraconimidophenoxy)phenyl]propane, bis(3,5-dimethyl-4-citraconimidophenyl)methane, bis(3-ethyl-5-methyl-4-citraconimidophenyl)methane, bis(3,5-diethyl-4-citraconimidophenyl)methane, polyphenylmethanemaleimide, fluorescein-5-maleimide, as well as a prepolymer of these maleimide compounds, or a prepolymer of maleimide compounds and amine compounds. One of these maleimide compounds (E) can be used, or two or more thereof can be appropriately mixed and used.

When the resin composition contains the bismaleimide compound (B) and the maleimide compound (C), the content of the maleimide compound (E) is preferably 1 to 50 parts by mass, more preferably 1 to 40 parts by mass, and still more preferably 1 to 30 parts by mass based on 100 parts by mass of the total of the bismaleimide compound (B) and the maleimide compound (C), from the viewpoint of exhibiting excellent photocurability.

[Filler (F)]

In the resin composition of the present embodiment, a filler (F) (also referred to as component (F)) can be used for improving a variety of characteristics such as a coating property and heat resistance. The filler (F) is preferably one that has an insulation property and does not inhibit transmittivity for various active energy rays used for photocuring, and more preferably one that does not inhibit transmittivity for active energy rays including a wavelength of 365 nm (i-line) and/or a wavelength of 405 nm (h-line).

Examples of the filler (F) include, for example, silica (for example, natural silica, fused silica, amorphous silica and hollow silica), an aluminum compound (for example, boehmite, aluminum hydroxide, alumina and aluminum nitride), a boron compound (for example, boron nitride), a magnesium compound (for example, magnesium oxide and magnesium hydroxide), a calcium compound (for example, calcium carbonate), a molybdenum compound (for example, molybdenum oxide and zinc molybdate), a barium compound (for example, barium sulfate and barium silicate), talc (for example, natural talc and calcined talc), mica, glass (for example, short fibrous glass, spherical glass, fine powder glass, E glass, T glass and D glass), silicone powder, a fluororesin-based filler, a urethane resin-based filler, a (meth)acrylic resin-based filler, a polyethylene-based filler, a styrene-butadiene rubber, and a silicone rubber. One of these fillers (F) can be used, or two or more thereof can be appropriately mixed and used.

Among the above, it is preferable that the filler (D) should be one or more selected from the group consisting of silica, boehmite, barium sulfate, silicone powder, a fluororesin-based filler, a urethane resin-based filler, a (meth)acrylic resin-based filler, a polyethylene-based filler, a styrene-butadiene rubber, and a silicone rubber.

These fillers (F) may be surface-treated with a silane coupling agent, which will be mentioned later, or the like.

From the viewpoint of improving the heat resistance of the cured product and also obtaining a good coating property, silica is preferable and fused silica is more preferable. Specific examples of the silica include SFP-130MC (trade name) manufactured by Denka Company Limited, and SC2050-MB (trade name), SC1050-MLE (trade name), YA010C-MFN (trade name), and YA050C-MJA (trade name) manufactured by Admatechs Company Limited.

The particle diameter of the filler (F) is not particularly limited, but from the viewpoint of ultraviolet light transmissivity of the resin composition, it is normally 0.005 to 10 μm, and is preferably 0.01 to 1.0 μm.

In the resin composition, the content of the filler (F) is usually preferably 300 parts by mass or less, more preferably 200 parts by mass or less, and still more preferably 100 parts by mass or less based on 100 parts by mass of the resin solid content in the resin composition from the viewpoint of making the light transmissivity of the resin composition and the heat resistance of the cured product good. When the filler is contained, the lower limit value of its content is usually 1 part by mass based on 100 parts by mass of the resin solid content in the resin composition, from the viewpoint of obtaining effects of improving a variety of characteristics such as a coating property and heat resistance.

[Silane Coupling Agent and Wetting and Dispersing Agent]

In the resin composition in the present embodiment, a silane coupling agent and/or a wetting and dispersing agent can also be used in combination in order to improve the dispersibility of the filler, and the adhesive strength between the polymers and/or the resins and the filler.

The silane coupling agent is not particularly limited as long as it is a silane coupling agent generally used for surface treatment of inorganic matters. Specific examples include aminosilane-based compounds such as 3-aminopropyltrimethoxysilane, γ-aminopropyltriethoxysilane, 3-aminopropyldimethoxysilane, 3-aminopropyldiethoxymethylsilane, N-β-(aminoethyl)-γ-aminopropyltrimethoxysilane, N-(2-aminoethyl)-3-aminopropyltriethoxysilane, N-(2-aminoethyl)-3-aminopropyldimethoxymethylsilane, N-(2-aminoethyl)-3-aminopropyldiethoxymethylsilane, N-phenyl-3-aminopropyltrimethoxysilane, N-phenyl-3-aminopropyltriethoxysilane, [3-(6-aminohexylamino)propyl]trimethoxysilane and [3-(N,N-dimethylamino)propyl]trimethoxysilane; epoxysilane-based compounds such as γ-glycidoxypropyltrimethoxysilane, 3-glycidoxypropyltriethoxysilane, 3-glycidoxypropyldimethoxysilane, 3-glycidoxypropyldiethoxymethylsilane, 2-(3,4-epoxycyclohexyl)ethyltrimethoxysilane and [8-(glycidyloxy)-n-octyl]trimethoxysilane; vinylsilane-based compounds such as vinyltris(2-methoxyethoxy)silane, vinyltrimethoxysilane, vinyltriethoxysilane, dimethoxymethylvinylsilane, diethoxymethylvinylsilane, trimethoxy(7-octen-1-yl)silane and trimethoxy(4-vinylphenyl)silane; methacrylic silane-based compounds such as 3-methacryloxypropyltrimethoxysilane, 3-methacryloxypropyltriethoxysilane, 3-methacryloxypropyldimethoxymethylsilane and 3-methacryloxypropyldiethoxymethylsilane; acrylic silane-based compounds such as 3-acryloxypropyltrimethoxysilane and 3-acryloxypropyltriethoxysilane; isocyanate silane-based compounds such as 3-isocyanatepropyltrimethoxysilane and 3-isocyanatepropyltriethoxysilane; isocyanurate silane-based compounds such as tris-(trimethoxysilylpropyl)isocyanurate; mercaptosilane-based compounds such as 3-mercaptopropyltrimethoxysilane and 3-mercaptopropyldimethoxymethylsilane; ureidosilane-based compounds such as 3-ureidopropyltriethoxysilane; styrylsilane-based compounds such as p-styryltrimethoxysilane; cationic silane-based compounds such as N-β-(N-vinylbenzylaminoethyl)-γ-aminopropyltrimethoxysilane hydrochlorides; acid anhydride-based compounds such as [3-(trimethoxysilyl)propyl]succinic anhydride; phenylsilane-based compounds such as phenyltrimethoxysilane, phenyltriethoxysilane, dimethoxymethylphenylsilane, diethoxymethylphenylsilane and p-tolyltrimethoxysilane; and arylsilane-based compounds such as trimethoxy(1-naphthyl)silane. One of these silane coupling agents can be used, or two or more thereof can be appropriately mixed and used.

In the resin composition, the content of the silane coupling agent is usually 0.1 to 10 parts by mass based on 100 parts by mass of the resin solid content in the resin composition.

The wetting and dispersing agent is not particularly limited as long as it is a dispersion stabilizer used for a paint. Specific examples of the wetting and dispersing agent include a wetting and dispersing agent such as DISPERBYK®-110 (trade name), 111 (trade name), 118 (trade name), 180 (trade name), and 161 (trade name), BYK®-W996 (trade name), W9010 (trade name), and W903 (trade name) manufactured by BYK Japan KK. One of these wetting and dispersing agents can be used, or two or more thereof can be appropriately mixed and used.

In the resin composition, the content of the wetting and dispersing agent is usually 0.1 to 10 parts by mass based on 100 parts by mass of the resin solid content in the resin composition.

[Cyanate Compound, Phenolic Resin, Oxetane Resin, Benzoxazine Compound, Epoxy Resin, and Additional Compound]

In the present embodiment, it is possible to use a variety of types of compounds and resins such as a cyanate compound, a phenolic resin, an oxetane resin, a benzoxazine compound, epoxy resin and additional compounds in addition to the compound (A), the bismaleimide compound (B), the maleimide compound (C), the photo initiator (D), and the maleimide compound (E) according to the present embodiment, depending on properties such as flame retardancy, heat resistance and a thermal expansion property of the cured product, as long as the effect of the present invention is achieved. Preferably, these compounds and resins ensure that the resin composition becomes light-sensitive to be photocured when exposed with an active energy ray including a wavelength of 365 nm (i-line) and/or an active energy ray including a wavelength of 405 nm (h-line).

One of these compounds and resins can be used, or two or more thereof can be appropriately mixed and used.

<Cyanate Compound>

The cyanate compound is not particularly limited as long as it is a resin having in the molecule an aromatic moiety substituted by at least one cyanate group (cyanate group).

For example, mention may be made of those represented by the formula (27).

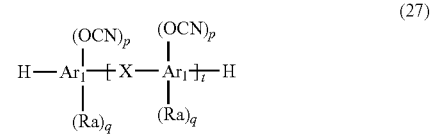

(27)

In the formula (27), $Ar_1$ represents a benzene ring, a naphthalene ring, or two benzene rings bonded to each other by a single bond. When there are a plurality of $Ar_1$, $Ar_1$ may be the same as or different from each other. Each Ra independently represents a hydrogen atom, an alkyl group having 1 to 6 carbon atoms, an alkenyl group having 2 to 6 carbon atoms, an aryl group having 6 to 12 carbon atoms, an alkoxy group having 1 to 4 carbon atoms, or a group in which an alkyl group having 1 to 6 carbon atoms and an aryl group having 6 to 12 carbon atoms are bonded to each other. The aromatic ring for Ra may have a substituent, and any position can be selected for the substituents in $Ar_1$ and Ra. p represents the number of cyanate groups bonded to $Ar_1$ and is each independently an integer of 1 to 3. q represents the number of Ra bonded to $Ar_1$ and is 4-p when $Ar_1$ is a benzene ring, 6-p when $Ar_1$ is a naphthalene ring, and 8-p when $Ar_1$ is two benzene rings bonded to each other by a single bond. t represents the average number of repetitions and is an integer of 0 to 50, and the cyanate compound may be a mixture of compounds having different t. X represents any of a single bond, a divalent organic group having 1 to 50 carbon atoms (a hydrogen atom may be replaced by a heteroatom), a divalent organic group having 1 to 10 nitrogen atoms (for example, —N—R—N— (wherein R represents an organic group)), a carbonyl group (—CO—), a carboxy group (—C(═O)O—), a carbonyl dioxide group (—OC(═O)O—), a sulfonyl group (—SO$_2$—), a divalent sulfur atom, and a divalent oxygen atom, and X is each independently as defined above when there are a plurality of X.

The alkyl group for Ra in the formula (27) may have either a linear or branched chain structure or a cyclic structure (for example, a cycloalkyl group).

In addition, a hydrogen atom in the alkyl group and the aryl group for Ra in the formula (27) may be replaced by a halogen atom such as a fluorine atom or a chlorine atom; an alkoxyl group such as a methoxy group or a phenoxy group; a cyano group, or the like.

Specific examples of the alkyl group include a methyl group, an ethyl group, a propyl group, an isopropyl group, a n-butyl group, an isobutyl group, a tert-butyl group, a n-pentyl group, a 1-ethylpropyl group, a 2,2-dimethylpropyl group, a cyclopentyl group, a hexyl group, a cyclohexyl group, and a trifluoromethyl group.

Specific examples of the alkenyl group include a vinyl group, a (meth)allyl group, an isopropenyl group, a 1-propenyl group, a 2-butenyl group, a 3-butenyl group, a 1,3-butanedienyl group, a 2-methyl-2-propenyl group, a 2-pentenyl group, and a 2-hexenyl group.

Specific examples of the aryl group include a phenyl group, a xylyl group, a mesityl group, a naphthyl group, a phenoxyphenyl group, an ethylphenyl group, an o-, m-, or p-fluorophenyl group, a dichlorophenyl group, a dicyanophenyl group, a trifluorophenyl group, a methoxyphenyl group, and an o-, m-, or p-tolyl group.

Examples of the alkoxyl group include a methoxy group, an ethoxy group, a propoxy group, an isopropoxy group, a n-butoxy group, an isobutoxy group, and a tert-butoxy group.

Specific examples of the divalent organic group having 1 to 50 carbon atoms for X in the formula (27) include a methylene group, an ethylene group, a trimethylene group, a cyclopentylene group, a cyclohexylene group, a trimethylcyclohexylene group, a biphenylylmethylene group, a dimethylmethylene-phenylene-dimethylmethylene group, a fluorenediyl group, and a phthalidediyl group. A hydrogen atom in the divalent organic group may be replaced by a halogen atom such as a fluorine atom or a chlorine atom; an alkoxyl group such as a methoxy group or a phenoxy group; a cyano group, or the like.

Examples of the divalent organic group having 1 to 10 nitrogen atoms for X in the formula (27) include an imino group and a polyimide group.

Examples of the organic group of X in the formula (27) include those having a structure represented by the formula (28) or those having a structure represented by the formula (29).

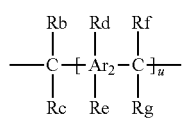

(28)

In the formula (28), Ar$_2$ represents a benzenediyl group, a naphthalenediyl group, or a biphenyldiyl group, and may be the same as or different from each other when u is an integer of 2 or more. Rb, Rc, Rf, and Rg each independently represent a hydrogen atom, an alkyl group having 1 to 6 carbon atoms, an aryl group having 6 to 12 carbon atoms, a trifluoromethyl group, or an aryl group having at least one phenolic hydroxy group. Rd and Re are each independently selected from any one of a hydrogen atom, an alkyl group having 1 to 6 carbon atoms, an aryl group having 6 to 12 carbon atoms, an alkoxyl group having 1 to 4 carbon atoms, and a hydroxy group. u is an integer of 0 to 5.

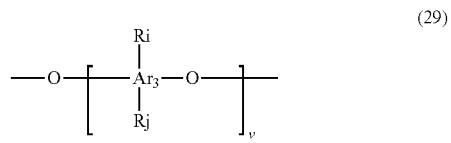

(29)

In the formula (29), Ar$_3$ represents a benzenediyl group, a naphthalenediyl group, or a biphenyldiyl group, and may be the same as or different from each other when v is an integer of 2 or more. Ri and Rj each independently represent a hydrogen atom, an alkyl group having 1 to 6 carbon atoms, an aryl group having 6 to 12 carbon atoms, a benzyl group, an alkoxyl group having 1 to 4 carbon atoms, a hydroxy group, a trifluoromethyl group, or an aryl group substituted by at least one cyanate group. v represents an integer of 0 to 5, and the cyanate compound may be a mixture of compounds having different v.

Furthermore, examples of X in the formula (27) include divalent groups represented by the following formulas.

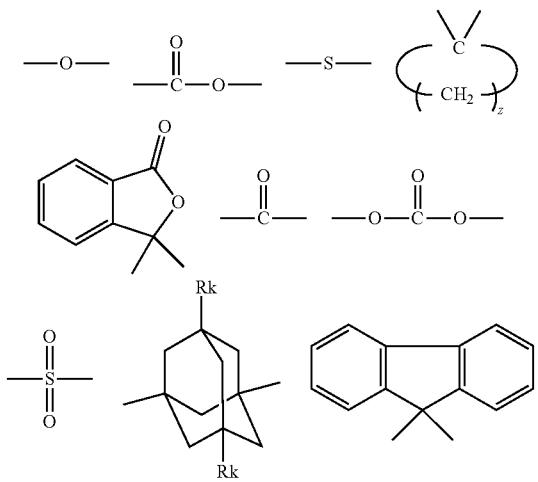

Here, in the above formula, z represents an integer of 4 to 7. Each Rk independently represents a hydrogen atom or an alkyl group having 1 to 6 carbon atoms.

Specific examples of Ar$_2$ in the formula (28) and Ar$_3$ in the formula (29) include a benzenediyl group to which two carbon atoms shown in the formula (28) or two oxygen atoms shown in the formula (29) are bonded at positions 1 and 4 or positions 1 and 3, a biphenyldiyl group to which the above two carbon atoms or two oxygen atoms are bonded at positions 4 and 4', positions 2 and 4', positions 2 and 2', positions 2 and 3', positions 3 and 3', or positions 3 and 4', and a naphthalenediyl group to which the above two carbon atoms or two oxygen atoms are bonded at positions 2 and 6, positions 1 and 5, positions 1 and 6, positions 1 and 8, positions 1 and 3, positions 1 and 4, or positions 2 and 7.

The alkyl group and the aryl group for Rb, Rc, Rd, Re, Rf, and Rg in the formula (28) and Ri and Rj in the formula (29) have the same meanings as those in the formula (27).

Specific examples of the cyanato-substituted aromatic compound represented by the formula (27) include cyanatobenzene, 1-cyanato-2-, 1-cyanato-3-, or 1-cyanato-4-methylbenzene, 1-cyanato-2-, 1-cyanato-3-, or 1-cyanato-4- methoxybenzene, 1-cyanato-2,3-, 1-cyanato-2,4-, 1-cyanato-2,5-, 1-cyanato-2,6-, 1-cyanato-3,4-, or 1-cyanato-3,5-dimethylbenzene, cyanatoethylbenzene, cyanatobutylbenzene, cyanatooctylbenzene, cyanatononylbenzene, 2-(4-cyanatophenyl)-2-phenylpropane (a cyanate of 4-α-cumylphenol), 1-cyanato-4-cyclohexylbenzene, 1-cyanato-4-vinylbenzene, 1-cyanato-2- or 1-cyanato-3-chlorobenzene, 1-cyanato-2,6-dichlorobenzene, 1-cyanato-2-methyl-3-chlorobenzene, cyanatonitrobenzene, 1-cyanato-4-nitro-2-ethylbenzene, 1-cyanato-2-methoxy-4-allylbenzene (a cyanate of eugenol), methyl(4-cyanatophenyl)sulfide, 1-cyanato-3-trifluoromethylbenzene, 4-cyanatobiphenyl, 1-cyanato-2- or 1-cyanato-4-acetylbenzene, 4-cyanatobenzaldehyde, methyl 4-cyanatobenzoate ester, phenyl 4-cyanatobenzoate ester, 1-cyanato-4-acetaminobenzene, 4-cyanatobenzophenone, 1-cyanato-2,6-di-tert-butylbenzene, 1,2-dicyanatobenzene, 1,3-dicyanatobenzene, 1,4-dicyanatobenzene, 1,4-dicyanato-2-tert-butylbenzene, 1,4-dicyanato-2,4-dimethylbenzene, 1,4-dicyanato-2,3,4-dimethylbenzene, 1,3-dicyanato-2,4,6-trimethylbenzene, 1,3-dicyanato-5-methylbenzene, 1-cyanato- or 2-cyanatonaphthalene, 1-cyanato-4-methoxynaphthalene, 2-cyanato-6-methylnaphthalene, 2-cyanato-7-methoxynaphthalene, 2,2'-dicyanato-1,1'-binaphthyl, 1,3-, 1,4-, 1,5-, 1,6-, 1,7-, 2,3-, 2,6-, or 2,7-dicyanatonaphthalene, 2,2'- or 4,4'-dicyanatobiphenyl, 4,4'-dicyanatooctafluorobiphenyl, 2,4'- or 4,4'-dicyanatodiphenylmethane, bis(4-cyanato-3,5-dimethylphenyl)methane, 1,1-bis(4-cyanatophenyl)ethane, 1,1-bis(4-cyanatophenyl)propane, 2,2-bis(4-cyanatophenyl)propane, 2,2-bis(4-cyanato-3-methylphenyl)propane, 2,2-bis(2-cyanato-5-biphenylyl)propane, 2,2-bis(4-cyanatophenyl)hexafluoropropane, 2,2-bis(4-cyanato-3,5-dimethylphenyl)propane, 1,1-bis(4-cyanatophenyl)butane, 1,1-bis(4-cyanatophenyl)isobutane, 1,1-bis(4-cyanatophenyl)pentane, 1,1-bis(4-cyanatophenyl)-3-methylbutane, 1,1-bis(4-cyanatophenyl)-2-methylbutane, 1,1-bis(4-cyanatophenyl)-2,2-dimethylpropane, 2,2-bis(4-cyanatophenyl)butane, 2,2-bis(4-cyanatophenyl)pentane, 2,2-bis(4-cyanatophenyl)hexane, 2,2-bis(4-cyanatophenyl)-3-methylbutane, 2,2-bis(4-cyanatophenyl)-4-methylpentane, 2,2-bis(4-cyanatophenyl)-3,3-dimethylbutane, 3,3-bis(4-cyanatophenyl)hexane, 3,3-bis(4-cyanatophenyl)heptane, 3,3-bis(4-cyanatophenyl)octane, 3,3-bis(4-cyanatophenyl)-2-methylpentane, 3,3-bis(4-cyanatophenyl)-2-methylhexane, 3,3-bis(4-cyanatophenyl)-2,2-dimethylpentane, 4,4-bis(4-cyanatophenyl)-3-methylheptane, 3,3-bis(4-cyanatophenyl)-2-methylheptane, 3,3-bis(4-cyanatophenyl)-2,2-dimethylhexane, 3,3-bis(4-cyanatophenyl)-2,4-dimethylhexane, 3,3-bis(4-cyanatophenyl)-2,2,4-trimethylpentane, 2,2-bis(4-cyanatophenyl)-1,1,1,3,3,3-hexafluoropropane, bis(4-cyanatophenyl)phenylmethane, 1,1-bis(4-cyanatophenyl)-1-phenylethane, bis(4-cyanatophenyl)biphenylmethane, 1,1-bis(4-cyanatophenyl)cyclopentane, 1,1-bis(4-cyanatophenyl)cyclohexane, 2,2-bis(4-cyanato-3-isopropylphenyl)propane, 1,1-bis(3-cyclohexyl-4-cyanatophenyl)cyclohexane, bis(4-cyanatophenyl)diphenylmethane, bis(4-cyanatophenyl)-2,2-dichloroethylene, 1,3-bis[2-(4-cyanatophenyl)-2-propyl]benzene, 1,4-bis[2-(4-cyanatophenyl)-2-propyl]benzene, 1,1-bis(4-cyanatophenyl)-3,3,5-trimethylcyclohexane, 4-[bis(4-cyanatophenyl)methyl]biphenyl, 4,4-dicyanatobenzophenone, 1,3-bis(4-cyanatophenyl)-2-propen-1-one, bis(4-cyanatophenyl) ether, bis(4-cyanatophenyl) sulfide, bis(4-cyanatophenyl) sulfone, 4-cyanatobenzoic acid-4-cyanatophenyl ester (4-cyanatophenyl-4-cyanatobenzoate), bis-(4-cyanatophenyl) carbonate, 1,3-bis(4-cyanatophenyl)adamantane, 1,3-bis(4-cyanatophenyl)-5,7-dimethyladamantane, 3,3-bis(4-cyanatophenyl)isobenzofuran-1(3H)-one (a cyanate of phenolphthalein), 3,3-bis(4-cyanato-3-methylphenyl)isobenzofuran-1(3H)-one (a cyanate of o-cresolphthalein), 9,9'-bis(4-cyanatophenyl)fluorene, 9,9-bis(4-cyanato-3-methylphenyl)fluorene, 9,9-bis(2-cyanato-5-biphenylyl)fluorene, tris(4-cyanatophenyl)methane, 1,1,1-tris(4-cyanatophenyl)ethane, 1,1,3-tris(4-cyanatophenyl)propane, α,α,α'-tris(4-cyanatophenyl)-1-ethyl-4-isopropylbenzene, 1,1,2,2-tetrakis(4-cyanatophenyl)ethane, tetrakis(4-cyanatophenyl)methane, 2,4,6-tris(N-methyl-4-cyanatoanilino)-1,3,5-triazine, 2,4-bis(N-methyl-4-cyanatoanilino)-6-(N-methylanilino)-1,3,5-triazine, bis(N-4-cyanato-2-methylphenyl)-4,4'-oxydiphthalimide, bis(N-3-cyanato-4-methylphenyl)-4,4'-oxydiphthalimide, bis(N-4-cyanatophenyl)-4,4'-oxydiphthalimide, bis(N-4-cyanato-2-methylphenyl)-4,4'-(hexafluoroisopropylidene)diphthalimide, tris(3,5-dimethyl-4-cyanatobenzyl) isocyanurate, 2-phenyl-3,3-bis(4-cyanatophenyl)phthalimidine, 2-(4-methylphenyl)-3,3-bis(4-cyanatophenyl)phthalimidine, 2-phenyl-3,3-bis(4-cyanato-3-methylphenyl)phthalimidine, 1-methyl-3,3-bis(4-cyanatophenyl)indolin-2-one, and 2-phenyl-3,3-bis(4-cyanatophenyl)indolin-2-one.

One of these cyanate compounds can be used, or two or more thereof can be appropriately mixed and used.

Other specific examples of the cyanate compound represented by the formula (27) include those obtained by cyanation of a phenolic resin such as a phenol novolac resin and a cresol novolac resin (those obtained by reacting phenol, an alkyl-substituted phenol or a halogen-substituted phenol with a formaldehyde compound such as formalin or paraformaldehyde in an acidic solution, using a publicly known method), a trisphenol novolac resin (those obtained by reacting hydroxybenzaldehyde with phenol in the presence of an acidic catalyst), a fluorene novolac resin (those obtained by reacting a fluorenone compound with a 9,9-bis(hydroxyaryl)fluorene in the presence of an acidic catalyst), a phenol aralkyl resin, a cresol aralkyl resin, a naphthol aralkyl resin, and a biphenyl aralkyl resin (those obtained by reacting a bishalogenomethyl compound as represented by $Ar_4$—$(CH_2Y)_2$ (wherein $Ar_4$ represents a phenyl group and Y represents a halogen atom. The same applies in this paragraph) with a phenolic compound with an acidic catalyst or with no catalyst using a publicly known method, those obtained by reacting a bis(alkoxymethyl) compound as represented by $Ar_4$—$(CH_2OR)_2$ (wherein R represents an alkyl group) with a phenolic compound in the presence of an acidic catalyst, or those obtained by reacting a bis(hydroxymethyl) compound as represented by $Ar_4$—$(CH_2OH)_2$ with a phenolic compound in the presence of an acidic catalyst, or those obtained by polycondensing an aromatic aldehyde compound, an aralkyl compound, and a phenolic compound, using a publicly known method), a phenol-modified xylene formaldehyde resin (those obtained by reacting a xylene formaldehyde resin with a phenolic compound in the presence of an acidic catalyst, using a publicly known method), a modified naphthalene formaldehyde resin (those obtained by reacting a naphthalene formaldehyde resin with a hydroxy-substituted aromatic compound in the presence of an acidic catalyst, using a publicly known method), a phenol-modified dicyclopentadiene resin, or a phenolic resin having a polynaphthylene ether structure (those obtained by subjecting a polyvalent hydroxynaphthalene compound having two or more phenolic hydroxy groups in one molecule to dehydration condensation in the presence of a basic catalyst, using a publicly known method)

by a method similar to the above, and a prepolymer thereof. One of these cyanate compounds can be used, or two or more thereof can be appropriately mixed and used.

The method for producing these cyanate compounds is not particularly limited, and a publicly known method can be used. Specific examples thereof include acquisition or synthesis of a hydroxy group containing compound having a desired backbone and cyanation of that compound by modifying the hydroxy group by a publicly known method. Examples of the approach for the cyanation of hydroxy groups include, for example, the approach described in Ian Hamerton, "Chemistry and Technology of Cyanate Ester Resins," Blackie Academic & Professional.

The cured product using these cyanate compounds has a property of being excellent in glass transition temperature, a low thermal expansion property, plating adhesiveness, and the like.

When the resin composition contains the bismaleimide compound (B) and the maleimide compound (C), the content of the cyanate compound is 0.01 to 40 parts by mass based on 100 parts by mass of the total of the bismaleimide compound (B) and the maleimide compound (C).

<Phenolic Resin>

As the phenolic resin, those publicly known in general can be used as long as they are phenolic resins having two or more hydroxyl groups in one molecule. Examples thereof include a bisphenol A-based phenolic resin, a bisphenol E-based phenolic resin, a bisphenol F-based phenolic resin, a bisphenol S-based phenolic resin, a phenol novolac resin, a bisphenol A novolac-based phenolic resin, a glycidyl ester-based phenolic resin, an aralkyl novolac-based phenolic resin, a biphenyl aralkyl-based phenolic resin, a cresol novolac-based phenolic resin, a polyfunctional phenolic resin, a naphthol resin, a naphthol novolac resin, a polyfunctional naphthol resin, an anthracene-based phenolic resin, a naphthalene backbone modified novolac-based phenolic resin, a phenol aralkyl-based phenolic resin, a naphthol aralkyl-based phenolic resin, a dicyclopentadiene-based phenolic resin, a biphenyl-based phenolic resin, an alicyclic phenolic resin, a polyol-based phenolic resin, a phosphorus containing phenolic resin, a polymerizable unsaturated hydrocarbon group containing phenolic resin, and a hydroxyl group containing silicone resin. One of these phenolic resins can be used, or two or more thereof can be appropriately mixed and used.

When the resin composition contains the bismaleimide compound (B) and the maleimide compound (C), the content of the phenolic resin is 0.01 to 40 parts by mass based on 100 parts by mass of the total of the bismaleimide compound (B) and the maleimide compound (C).

<Oxetane Resin>

As the oxetane resin, those publicly known in general can be used. Examples thereof include, for example, oxetane, an alkyloxetane such as 2-methyloxetane, 2,2-dimethyloxetane, 3-methyloxetane, and 3,3-dimethyloxetane, 3-methyl-3-methoxymethyloxetane, 3,3-di(trifluoromethyl)perfluorooxetane, 2-chloromethyloxetane, 3,3-bis(chloromethyl)oxetane, biphenyl-based oxetane, OXT-101 (manufactured by Toagosei Co., Ltd., product name), OXT-121 (manufactured by Toagosei Co., Ltd., product name), and OXT-221 (manufactured by Toagosei Co., Ltd., product name). One of these oxetane resins can be used, or two or more thereof can be appropriately mixed and used.

When the resin composition contains the bismaleimide compound (B) and the maleimide compound (C), the content of the oxetane resin is 0.01 to 40 parts by mass based on 100 parts by mass of the total of the bismaleimide compound (B) and the maleimide compound (C).

<Benzoxazine Compound>

As the benzoxazine compound, those publicly known in general can be used as long as they are compounds having two or more dihydrobenzoxazine rings in one molecule. Examples thereof include a bisphenol A-based benzoxazine BA-BXZ (manufactured by Konishi Chemical Ind. Co., Ltd., product name), a bisphenol F-based benzoxazine BF-BXZ (manufactured by Konishi Chemical Ind. Co., Ltd., product name), a bisphenol S-based benzoxazine BS-BXZ (manufactured by Konishi Chemical Ind. Co., Ltd., product name), and a phenolphthalein-based benzoxazine. One of these benzoxazine compounds can be used, or two or more thereof can be appropriately mixed and used.

When the resin composition contains the bismaleimide compound (B) and the maleimide compound (C), the content of the benzoxazine compound is 0.01 to 40 parts by mass based on 100 parts by mass of the total of the bismaleimide compound (B) and the maleimide compound (C).

<Epoxy Resin>

There is no particular limitation on the epoxy resin, and those publicly known in general can be used. Examples thereof include, for example, a bisphenol A-based epoxy resin, a bisphenol E-based epoxy resin, a bisphenol F-based epoxy resin, a bisphenol S-based epoxy resin, a bisphenol A novolac-based epoxy resin, a biphenyl-based epoxy resin, a phenol novolac-based epoxy resin, a cresol novolac-based epoxy resin, a xylene novolac-based epoxy resin, a polyfunctional phenol-based epoxy resin, a naphthalene-based epoxy resin, a naphthalene backbone modified novolac-based epoxy resin, a naphthylene ether-based epoxy resin, a phenol aralkyl-based epoxy resin, an anthracene-based epoxy resin, a trifunctional phenol-based epoxy resin, a tetrafunctional phenol-based epoxy resin, triglycidyl isocyanurate, a glycidyl ester-based epoxy resin, an alicyclic epoxy resin, a dicyclopentadiene novolac-based epoxy resin, a biphenyl novolac-based epoxy resin, a phenol aralkyl novolac-based epoxy resin, a naphthol aralkyl novolac-based epoxy resin, an aralkyl novolac-based epoxy resin, a naphthol aralkyl-based epoxy resin, a dicyclopentadiene-based epoxy resin, a polyol-based epoxy resin, a phosphorus containing epoxy resin, a glycidyl amine, a compound obtained by epoxidizing a double bond of butadiene and the like, a compound obtained by the reaction between a hydroxyl group containing silicone resin and epichlorohydrin, and a halide thereof. One of these epoxy resins can be used, or two or more thereof can be appropriately mixed and used.

As the epoxy resin, commercially available products may be used, and examples thereof include an epoxy resin represented by the formula (30) (NC-3000 FH (product name) manufactured by Nippon Kayaku Co., Ltd., $n_5$ is about 4 in the formula (30)), and a naphthalene-based epoxy resin represented by the formula (31) (HP-4710 (product name) manufactured by DIC CORPORATION).

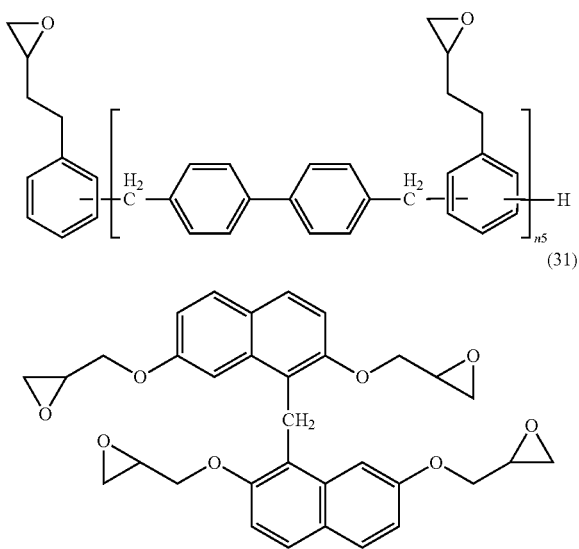

(30)

(31)

One of these epoxy resins can be used, or two or more thereof can be appropriately mixed and used.

When the resin composition contains the bismaleimide compound (B) and the maleimide compound (C), the content of the epoxy resin is 0.01 to 40 parts by mass based on 100 parts by mass of the total of the bismaleimide compound (B) and the maleimide compound (C).

<Additional Compound>

Examples of the additional compound include a vinyl ether such as ethyl vinyl ether, propyl vinyl ether, hydroxyethyl vinyl ether, and ethylene glycol divinyl ether; a styrene such as styrene, methylstyrene, ethylstyrene, and divinylbenzene; triallyl isocyanurate, trimethallyl isocyanurate, and bisallylnadic imide. One of these compounds can be used, or two or more thereof can be appropriately mixed and used.

When the resin composition contains the bismaleimide compound (B) and the maleimide compound (C), the content of the additional compound is 0.01 to 40 parts by mass based on 100 parts by mass of the total of the bismaleimide compound (B) and the maleimide compound (C).

[Organic Solvent]

The resin composition of the present embodiment may contain an organic solvent if required. When an organic solvent is used, the viscosity can be adjusted during the preparation of the resin composition. The type of the organic solvent is not particularly limited as long as it is capable of dissolving a part of or all of the resin in the resin composition. Examples of the organic solvent include halogen solvents such as dichloromethane, chloroform, dichloroethane, and chlorobenzene; aprotic polar solvents such as dimethylformamide, dimethylacetamide, dimethylsulfoxide, tetrahydrofuran, dioxane, and acetonitrile; ketone solvents such as acetone, methyl ethyl ketone, methyl isobutyl ketone, cyclopentanone, and cyclohexanone; cellosolve solvents such as 2-ethoxyethanol and propylene glycol monomethyl ether; aliphatic alcohol solvents such as methanol, ethanol, propanol, isopropanol, and butanol; aromatic group-containing phenol solvents such as phenol and cresol; ester solvents such as ethyl lactate, methyl acetate, ethyl acetate, butyl acetate, isoamyl acetate, methyl methoxypropionate, methyl hydroxyisobutyrate, γ-butyrolactone, and propylene glycol monomethyl ether acetate; and aromatic hydrocarbon solvents such as toluene and xylene.

Among these, an aprotic polar solvent, a ketone solvent, a cellosolve solvent, and an ester solvent are preferable from the viewpoint of exhibiting excellent solubility for the compound (A) and other resins and compounds, and an aprotic polar solvent, a ketone solvent, and an ester solvent are more preferable from the viewpoint of exhibiting superior solubility.

The aprotic polar solvent is preferably dimethylacetamide. The ketone solvent is preferably methyl ethyl ketone. The cellosolve solvent is preferably propylene glycol monomethyl ether. The ester solvent is preferably butyl acetate, γ-butyrolactone, or propylene glycol monomethyl ether acetate.

One of these organic solvents can be used, or two or more thereof can be appropriately mixed and used.

[Additional Component]

In the resin composition of the present embodiment, a variety of polymer compounds such as thermosetting resins, thermoplastic resins and oligomers thereof, and elastomers, which have not been mentioned before; flame retardant compounds, which have not been mentioned before; additive agents and the like can also be used in combination to the extent that the characteristics of the present embodiment are not impaired. These are not particularly limited as long as they are those generally used. Examples of the flame retardant compound include, for example, a nitrogen containing compound such as melamine and benzoguanamine, an oxazine ring containing compound, and a phosphorus compound such as a phosphate compound, an aromatic fused phosphate ester, and a halogen containing fused phosphate ester. Examples of the additive agent include, for example, an ultraviolet absorbing agent, an antioxidant, a fluorescent brightening agent, a photosensitizer, a dye, a pigment, a thickening agent, a lubricant, a defoaming agent, a surface conditioner, a brightening agent, a polymerization inhibitor and a thermal curing promoting agent. One of these components can be used, or two or more thereof can be appropriately mixed and used.

In the resin composition, the content of each of the additional components is usually 0.1 to 10 parts by mass based on 100 parts by mass of the resin solid content in the resin composition.

[Method for Producing Resin Composition and Varnish]

The resin composition of the present embodiment can be prepared by appropriately mixing the compound (A), if required, the bismaleimide compound (B), the maleimide compound (C), the photo initiator (D), the maleimide compound (E), a filler (F), the additional resin, the additional compound, the additive agent, and the like. Examples of the method for producing the resin composition include a method in which each of the components described above is sequentially compounded in a solvent and stirred sufficiently.

Upon producing the resin composition, publicly known treatment (stirring, mixing, and kneading treatment and the like) for uniformly dissolving or dispersing each component can be carried out, if required. Specifically, by using a stirring tank equipped with a stirrer having an appropriate stirring capacity to carry out the stirring and dispersion treatment, the dispersibility of each component such as the compound (A) in the resin composition can be improved. The stirring, mixing, and kneading treatment can be appropriately carried out by using a publicly known apparatus such as a stirring apparatus intended for dispersion such as an ultrasonic homogenizer; an apparatus intended for mixing such as a three roll mill, a ball mill, a bead mill, or a sand mill; or a revolution or rotation mixing apparatus. In addition, upon preparing the resin composition, an organic solvent can be used if required. The type of the organic solvent is not particularly limited as long as it is capable of dissolving the resin in the resin composition, and specific examples thereof are as described above.

The resin composition can be suitably used as a varnish upon fabricating a resin sheet of the present embodiment, which will be mentioned later. The varnish can be obtained by a publicly known method. For example, the varnish can be obtained by adding 10 to 900 parts by mass, and preferably 30 to 500 parts by mass of an organic solvent to 100 parts by mass of components other than the organic solvent in the resin composition and the publicly known treatment (stirring, mixing, kneading or the like). The organic solvent used for preparation of varnish is not particularly limited, and specific examples thereof are as described above.

[Application]

The resin composition of the present embodiment can be suitably used for the production of a multilayer printed wiring board, and can be preferably used for applications requiring an insulation resin composition. The resin composition of the present embodiment can be used for, for example, a photosensitive film, a photosensitive film with a support, a prepreg, a resin sheet, a circuit substrate (applications for a laminate, applications for a multilayer printed wiring board, and the like), a solder resist, an underfill material, a die bonding material, a semiconductor sealing material, a hole filling resin, a component embedding resin, or the like. Among them, the resin composition can be suitably used for an insulation layer of a multilayer printed wiring board or for a solder resist because of its excellent photocurable property and alkali developability.

[Cured Product]

A cured product is obtained by curing a resin composition. The cured product can be obtained by, for example, melting the resin composition or dissolving the resin composition in a solvent, then pouring the resin composition into a mold, and curing the resin composition with light under normal conditions. It is preferable to cure the resin composition in a light wavelength range of 100 to 500 nm where curing is efficiently promoted by a photo initiator or the like.

[Resin Sheet]

A resin sheet of the present embodiment is a resin sheet with a support containing: a support; and a resin layer disposed on one surface or both surfaces of the support, wherein the resin layer contains the resin composition of the present embodiment. The resin sheet can be produced by applying the resin composition onto the support and drying it. The resin layer in the resin sheet has excellent photocurability and alkaline developability.

As the support, those publicly known can be used and there is no particular limitation thereon, but it is preferably a resin film. Examples of the resin film include a polyimide film, a polyamide film, a polyester film, a polyethylene terephthalate (PET) film, a polybutylene terephthalate (PBT) film, a polypropylene (PP) film, a polyethylene (PE) film, a polyethylene naphthalate film, a polyvinyl alcohol film and a triacetyl acetate film. Among the above, PET film is preferable.

Preferably, the surface of the resin film is coated with a release agent in order to facilitate release from the resin layer. The thickness of the resin film is preferably in the range of 5 to 100 µm and more preferably in the range of 10 to 50 µm. When the thickness is less than 5 µm, the support tends to be easily torn at the time when the support is released before alkaline development, and when the thickness is greater than 100 µm, the resolution upon being exposed through the support tends to be reduced.

In addition, in order to reduce light scattering during exposure, it is preferable that the resin film should have excellent transparency.

Furthermore, in the resin sheet, the resin layer thereof may be protected with a protective film.

By protecting the resin layer side with a protective film, adhesion of dust and the like to the surface of the resin layer and scratches can be prevented. As the protective film, a film composed of a material similar to the resin film can be used. The thickness of the protective film is preferably in the range of 1 to 50 µm and more preferably in the range of 5 to 40 µm. If the thickness is less than 1 µm, the handleability of the protective film tends to be reduced, and if the thickness is greater than 50 µm, the inexpensiveness tends to be poor. Note that it is preferable for the protective film to have a smaller adhesive force between the resin layer and the protective film than the adhesive force between the resin layer and the support.

Examples of the method for producing the resin sheet include a method in which the resin composition is applied to a support such as PET film and the organic solvent is removed by drying to produce the resin sheet.

The application method can be carried out by a publicly known method using, for example, a roll coater, a comma coater, a gravure coater, a die coater, a bar coater, a lip coater, a knife coater, a squeeze coater, or the like. The drying can be carried out by, for example, a method of heating in a dryer at 60 to 200° C. for 1 to 60 minutes.

The amount of organic solvent remaining in the resin layer is preferably less than 5% by mass based on the total mass of the resin layer from the viewpoint of preventing diffusion of the organic solvent in the subsequent steps. It is preferable that the thickness of the resin layer should be 1 to 50 µm from the viewpoint of improving handleability.

The resin sheet can be preferably used for production of insulation layers of multilayer printed wiring boards.

[Multilayer Printed Wiring Board]

The multilayer printed wiring board in the present embodiment contains an insulation layer; and a conductor layer formed on one surface or both surfaces of the insulation layer, wherein the insulation layer contains the resin composition of the present embodiment. The insulation layer can also be obtained by, for example, laminating one or more of the resin sheets and curing them. The number of laminations in the insulation layer and the conductor layer can be appropriately set according to an intended application. The order of the insulation layer and the conductor layer is not particularly limited. The conductor layer may be a metal foil used for various printed wiring board materials, and examples thereof include metal foils of copper, aluminum and the like. Examples of the copper metal foil include a rolled copper foil and an electrolytic copper foil. The thickness of the conductor layer is normally 1 to 100 µm. In particular, it can be produced by the following method.

(Lamination Step)

In a lamination step, the resin layer side of the resin sheet is laminated to one surface or both surfaces of a circuit substrate using a vacuum laminator. Examples of the circuit substrate include, for example, a glass epoxy substrate, a metal substrate, a ceramic substrate, a silicon substrate, a semiconductor sealing resin substrate, a polyester substrate, a polyimide substrate, a BT resin substrate, and a thermosetting polyphenylene ether substrate. Note that a circuit substrate refers to a substrate in which a patterned conductor layer (circuit) is formed on one surface or both surfaces of a substrate as described above. Also, in a multilayer printed wiring board formed by alternately laminating a conductor layer and an insulation layer, a substrate in which one surface or both surfaces of the outermost layer of the multilayer printed wiring board are patterned conductor layers (circuits) is also included in the circuit substrate. Note that the insulation layer laminated on the multilayer printed wiring board may be an insulation layer obtained by laminating and curing one or more resin sheets in the present embodiment, or an insulation layer obtained by laminating one or more resin sheets in the present embodiment and one or more publicly known resin sheets different from the resin sheet in the present embodiment. Note that the mode in which the resin sheets in the present embodiment and the publicly known resin sheets different from the resin sheet in the present embodiment are laminated is not particularly limited. The surface of the conductor layer may be subjected to blackening treatment and/or roughening treatment by copper etching or the like in advance. In the lamination step, when the resin sheet has a protective film, the protective film is peeled off and removed. Then, the resin sheet and the circuit substrate are preheated if required, and while pressurizing and heating the resin layer of the resin sheet, it is crimped to the circuit substrate. In the present embodiment, a method of laminating the resin layer of the resin sheet to the circuit substrate under reduced pressure using a vacuum lamination method is suitably used.

As conditions of the lamination step, for example, it is preferable to perform the lamination under reduced pressure with a crimping temperature (lamination temperature) of 50 to 140° C., crimping pressure of 1 to 15 kgf/cm$^2$, crimping time of 5 to 300 seconds, and air pressure of 20 mmHg or less. Also, the lamination step may be in a batch type or in a continuous type using a roll. The vacuum lamination method can be carried out using a commercially available vacuum laminator. Examples of the commercially available vacuum laminator include, for example, a two-stage build-up laminator manufactured by Nikko-Materials Co., Ltd.

(Exposure Step)

In the exposure step, after providing the resin layer on the circuit substrate by the lamination step, a predetermined portion of the resin layer is irradiated with an active energy ray as a light source to cure the resin layer in the irradiated part. The compound (A) does not inhibit the photocuring reaction in the exposure step.

The irradiation may be performed through a mask pattern or may be performed by using the direct imaging method in which the irradiation is directly applied. Examples of the active energy ray include, for example, ultraviolet rays, visible rays of light, electron beam, and X-rays. The wavelength of the active energy ray is, for example, in the range of 200 to 600 nm. When an ultraviolet ray is used, the irradiation amount thereof is approximately 10 to 1000 mJ/cm$^2$. Upon producing a printed wiring board having a highly dense and highly detailed wiring formation (pattern) using the stepper exposure method, it is preferable to use, for example, an active energy ray including a wavelength of 365 nm (i-line) as an active energy ray. When an active energy ray including a wavelength of 365 nm (i-line) is used, the irradiation amount is approximately 10 to 10,000 mJ/cm$^2$. Upon producing a printed wiring board having a highly dense and highly detailed wiring formation (pattern) using the direct imaging method, it is preferable to use, for example, an active energy ray including a wavelength of 405 nm (h-line) as an active energy ray. When an active energy ray including a wavelength of 405 nm (h-line) is used, the irradiation amount is approximately 10 to 10,000 mJ/cm$^2$.

There are two exposure methods for passing through the mask pattern: the contact exposure method, in which the mask pattern is adhered to the multilayer printed wiring board, and the non-contact exposure method, in which parallel light rays are used to perform the exposure without adhering the mask pattern to the multilayer printed wiring board, but either method may be used. Also, when a support is present on the resin layer, it may be exposed from the top of the support, or it may be exposed after the support is removed.

(Alkaline Development Step)

When a support is not present on the resin layer, a portion which is not photocured directly in alkaline development (unexposed portion) is removed after the exposure step, and development is performed, whereby an insulation layer pattern can be formed.

When a support is present on the resin layer, the support is removed after the exposure step, and thereafter a portion which is not photocured in alkaline development (unexposed portion) is removed, and development is performed, whereby an insulation layer pattern can be formed.

The unexposed resin layer containing the resin composition of the present embodiment contains the compound (A) and thus has excellent alkaline developability and can rapidly remove the unexposed resin composition. Therefore, a printed wiring board having a highly detailed pattern can be obtained.

In the case of alkaline development, the developing solution is not particularly limited as long as unexposed portion is selectively eluted, and alkaline developing solutions such as an aqueous tetramethylammonium hydroxide solution, an aqueous sodium carbonate solution, an aqueous potassium carbonate solution, an aqueous sodium hydroxide solution and an aqueous potassium hydroxide solution are used. In the present embodiment, it is more preferable to use an aqueous tetramethylammonium hydroxide solution. One of these alkaline developing solutions can be used, or two or more thereof can be appropriately mixed and used.

As the alkaline development method, for example, a known method such as dipping, paddling, spraying, shaking immersion, blushing and scraping can be carried out. In pattern formation, these development methods can be used in combination if necessary. As the development method, use of a high-pressure spray is suitable because the resolution is further improved. When the spraying method is employed, the spray pressure is preferably 0.02 to 0.5 MPa.

(Postbaking Step) In the present embodiment, a postbaking step is carried out after the alkaline development step, thereby forming an insulation layer (cured product). Examples of the postbaking step include an ultraviolet irradiation step with a high pressure mercury lamp and a heating step using a clean oven, and these steps may be used in combination as well. When irradiating with ultraviolet ray, the irradiation amount thereof can be adjusted if required, and for example, the irradiation can be carried out at an irradiation amount of approximately 0.05 to 10 J/cm$^2$. Also, the conditions of heating can be appropriately selected if required, but they are preferably selected from the range of 20 to 180 minutes at 150 to 220° C., and more preferably from the range of 30 to 150 minutes at 160 to 200° C.

(Conductor Layer Formation Step)

After forming the insulation layer (cured product), a conductor layer is formed on the surface of the insulation layer by dry plating.

In forming the conductor layer, the surface modification treatment may be performed on the surface of the insulation layer before the dry plating. As the surface modification treatment, a known method such as plasma etching treatment, reverse sputtering treatment, or corona treatment can be used.

For the dry plating, a publicly known method such as a vapor deposition method, a sputtering method, and an ion plating method can be used. In the vapor deposition method (vacuum deposition method), for example, a metallic film can be formed on the insulation layer by placing the multilayer printed wiring board in a vacuum container and heating and evaporating the metal. In the sputtering method as well, for example, the multilayer printed wiring board is placed in a vacuum container, an inert gas such as argon is introduced, a direct current voltage is applied, the ionized inert gas is brought into collision with the target metal, and the knocked-out metal can be used to form a metallic film on the insulation layer.

Next, a conductor layer is formed by nonelectrolytic plating or electroplating. As a method of subsequent patterning, for example, a subtractive method, a semi-additive method, or the like can be used.

[Semiconductor Device]

A semiconductor device of the present embodiment contains the resin composition of the present embodiment. In particular, it can be produced by the following method. A semiconductor device can be produced by a mounting semiconductor chip at the conduction points on the multilayer printed wiring board. Here, the conduction points refer to the points in the multilayer printed wiring board where electrical signals are conveyed, and the locations thereof may be on the surface or at embedded points. In addition, the semiconductor chip is not particularly limited as long as they are electrical circuit elements made of semiconductors.

The method for mounting the semiconductor chip upon producing the semiconductor device is not particularly limited as long as the semiconductor chip effectively functions. Specific examples thereof include a wire bonding mounting method, a flip chip mounting method, a mounting method with a bumpless build-up layer (BBUL), a mounting method with an anisotropic conductive film (ACF), and a mounting method with a non-conductive film (NCF).

Alternatively, the semiconductor device can be produced by forming an insulation layer containing the resin composition on a semiconductor chip or a substrate on which semiconductor chip is mounted. The shape of the substrate on which semiconductor chip is mounted may be wafer-like or panel-like. After the formation, the semiconductor device can be produced using the same method as the multilayer printed wiring board described above.

EXAMPLES

The present embodiment will be more specifically described below using an Example and a Comparative Example. The present embodiment is not limited in any way by the following Example.

[Synthesis of Maleimide Compound (TMDM)]

Synthetic Example 1

A compound (TMDM) represented by the formula (20) was synthesized as follows.

[Synthesis of Amic Acid Compounds (Hereinafter Abbreviated as MA-TMDA.)]

First, MA-TMDA represented by the formula (32) was synthesized by the following method.

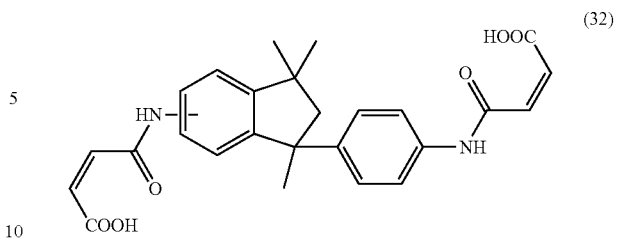

To a 100 mL four-necked flask equipped with an argon inlet, a Dean-Stark apparatus, a Dimroth condenser, and a thermometer, 5.2 g (53 mmol) of maleic anhydride, 20 mL of N-methylpyrrolidone (NMP), and 20 mL of toluene were added, and the mixture was stirred at room temperature (25° C.) under an argon stream to completely dissolve the maleic anhydride. To this solution were added 5.0 g (19 mmol) of TMDA (A mixture of 5-amino-1,3,3-trimethyl-1-(4-aminophenyl)-indane and 6-amino-1,3,3-trimethyl-1-(4-aminophenyl)-indane, manufactured by Nipponjunryo Chemicals Co., Ltd.) and 10 mL of NMP, and the mixture was stirred at room temperature (25° C.) for 17 hours.

A portion of the reaction solution was taken out, water and ethyl acetate were added thereto, and the mixture was shaken. Thereafter, the organic layer was taken out and dried over magnesium sulfate. The supernatant was evaporated at 40° C. to give a yellow oil. The $^1$H-NMR measurement was performed to confirm that the product was MA-TMDA represented by the formula (32).

The $^1$H-NMR attribution of MA-TMDA represented by the formula (32) is shown below. The $^1$H-NMR chart is shown in FIG. 1.

$^1$H-NMR (300 MHz, DMSO-d6) δ (ppm): 10.40 (m, 2H, —COOH), 7.30 (m, 7H, ArH), 6.33 (m, 4H, =CH—), 2.11 (m, 2H, —CH$_2$—), 1.48 (d, 3H, —CH$_3$), 1.21 (d, 3H, —CH$_3$), 0.92 (d, 3H, —CH$_3$)

[Synthesis of TMDM]

To the above reaction solution was added 0.67 g (3.5 mmol) of p-toluenesulfonic acid monohydrate, and heated to reflux at 127° C. for 2.5 hours. After cooling to room temperature (25° C.), the cooled reaction solution was poured into a mixed solution of 50 mL of saturated aqueous sodium hydrogen carbonate and 100 mL of ethyl acetate with stirring. Further, 100 mL of water and 100 mL of ethyl acetate were added thereto, stirred, and allowed to stand for 5 minutes. Thereafter, liquid separation was performed, and the aqueous layer was extracted 3 times with 50 mL of ethyl acetate. All organic layers were combined and washed once with 100 mL of water, once with 10 mL of saturated saline, and twice with 5 mL of saturated saline. After drying over magnesium sulfate and filtering off the solid, the solvent was distilled off at 40° C. to obtain yellow solid.

The resulting yellow solid was dissolved in 6.5 mL of acetone, and the acetone solution was poured into 300 mL of water. The precipitated solid was filtered off, washed with a small amount of isopropyl alcohol (IPA), and dried under reduced pressure at 50° C. for 20 hours to obtain 5.71 parts by mass of a yellow solid. The $^1$H-NMR measurement was performed to confirm that the product was the maleimide compound (TMDM) represented by the formula (20).

Figure 2:
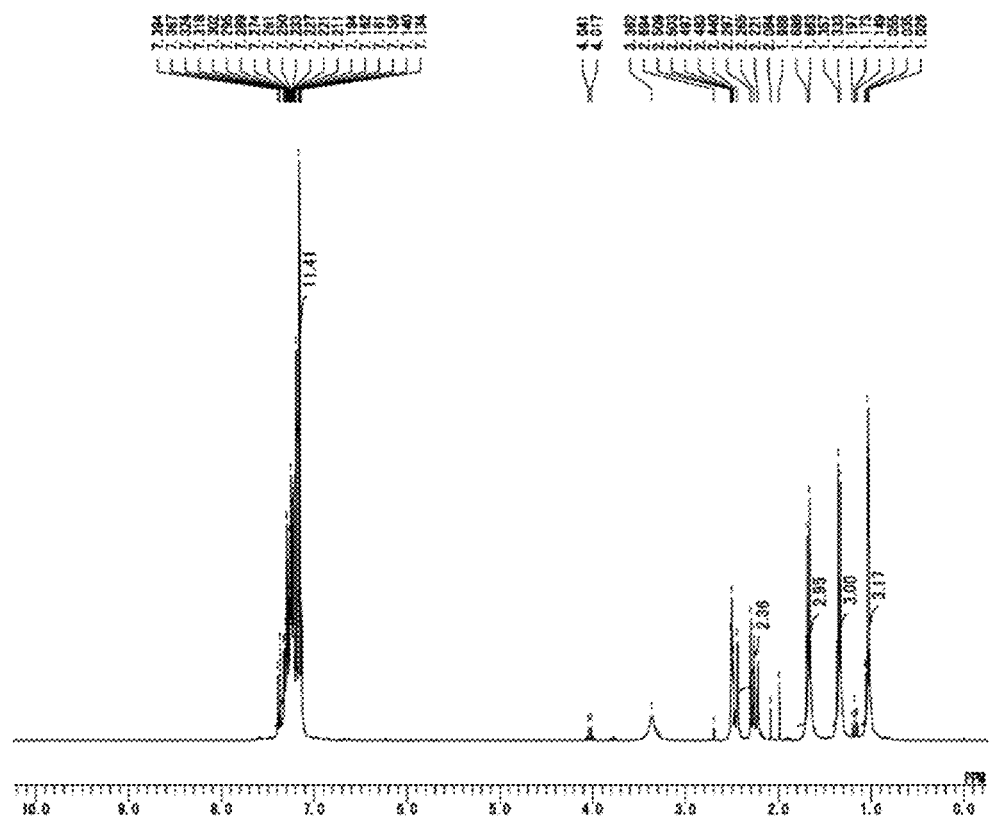
FIG. 2 is a $^1$H-NMR chart of an maleimide compound (TMDM).

The $^1$H-NMR attribution of TMDM is shown below. The $^1$H-NMR chart is shown in FIG. 2.

$^1$H-NMR (300 MHz, DMSO-d6) δ (ppm): 7.19 (m, 11H, ArH, —CH=CH—), 2.42 (m, 2H, —CH$_2$—), 1.66 (d, 3H, —CH$_3$), 1.32 (d, 3H, —CH$_3$), 1.00 (d, 3H, —CH$_3$)

[Synthesis of Compound Represented by Formula (16)]

Example 1

A compound represented by the formula (16) (also referred to as compound (A-1)) was synthesized as follows.

To a 200 mL flask were added 6.26 g (25 mmol) of ditrimethylolpropane (manufactured by Tokyo Kasei Kogyo Co., Ltd.), 20.81 g (105 mmol) of cyclohexane-1,2,4-tricarboxylic acid-1,2-anhydride (manufactured by Mitsubishi Gas Chemical Company, Inc., H-TMAn (trade name)), 3.05 g (25 mmol) of 4-dimethylaminopyridine, 11.13 g of triethylamine, and 70 g of dichloromethane, and the mixture was stirred at room temperature (25° C.) for 7 hours.

To the reaction solution were added 50 mL of water and 6 mL of methanol and stirred for 1 hour, then 50 mL of 5% hydrochloric acid was further added and stirred. Thereafter, liquid separation was performed, the aqueous layer was removed, and to the organic layer was added 350 mL of methyl ethyl ketone and 100 mL of 5% hydrochloric acid. The solution was transferred to a separation funnel, washed once with 150 mL of 5% hydrochloric acid and twice with 150 mL of water, dried over magnesium sulfate, and evaporated. Vacuum drying was performed at 130° C. to obtain 16.02 g of a white solid. As a result of $^1$H-NMR measurement, the obtained white solid was confirmed to be a compound (A-1) represented by the formula (16).

Figure 3:
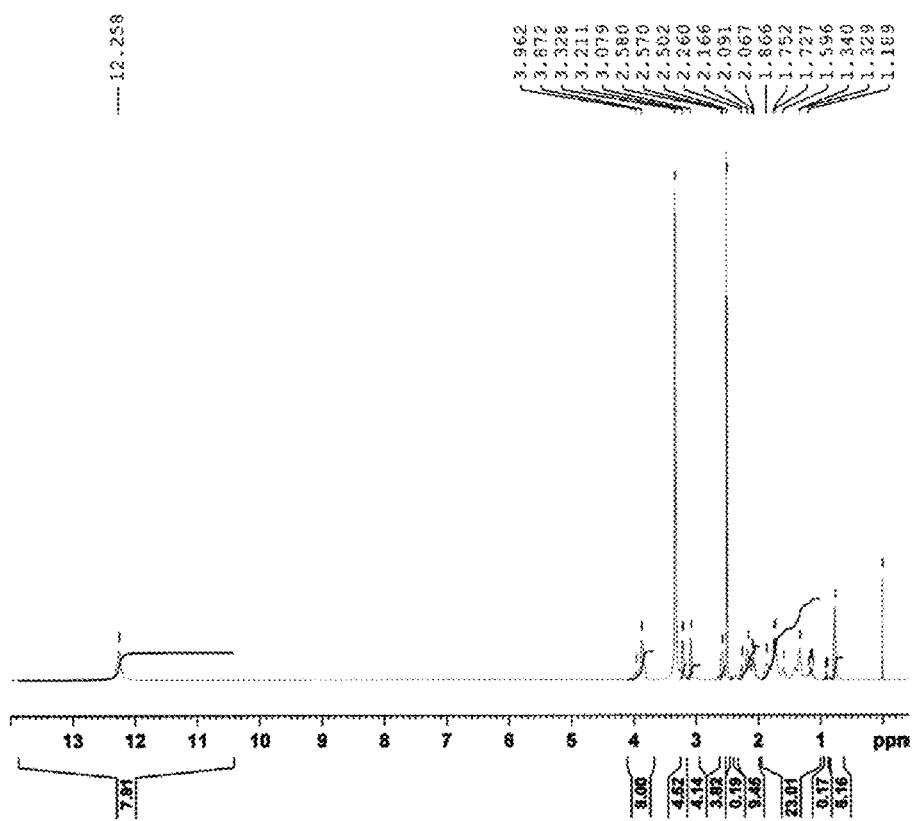
FIG. 3 is a $^1$H-NMR chart of a compound (A-1) obtained in Example 1.

The $^1$H-NMR attribution of the compound (A-1) is shown below. The $^1$H-NMR chart is shown in FIG. 3.

$^1$H-NMR (500 MHz, DMSO-d6) δ (ppm): 12.26 (s, 8H, —COOH), 3.87 (m, 8H), 3.21 (s, 4H), 3.08 (s, 4H), 2.58 (m, 4H), 2.3-2.0 (m, 9H), 1.9-1.0 (m, 23H), 0.77 (m, 6H)

In addition, the content of the compound (A-1) contained in the reaction solution obtained above was measured by the following method.

To 4500 mg of THF (tetrahydrofuran) was added 50 mg of the reaction solution to prepare the sample solution, which was subjected to GPC measurement under the following conditions. The peak area was calculated from the obtained elution curve, and the GPC area fraction (content) of each component contained in the reaction solution was calculated. The peak area was calculated from the area between the elution curve and the base line, and a peak that was not completely separated was calculated by vertical division.

(Measurement Conditions)

Measurement instrument: Prominence (trade name) manufactured by Shimadzu Corporation Column: KF-801 (trade name) manufactured by Showa Denko K.K., KF-802 (trade name) manufactured by Showa Denko K.K., KF-803 (trade name) manufactured by Showa Denko K.K., KF-804 (trade name) manufactured by Showa Denko K.K.

Flow rate: 1 mL/min

Column temperature: 40° C.

Detector: RI (Refractive Index) detector

As a result of GPC measurement, the content of the compound (A-1) contained in the reaction solution was 88%.

[Synthesis of Compound Represented by Formula (17)]

Example 2

A compound represented by the formula (17) (also referred to as compound (A-2)) was synthesized as follows.

To a 200 mL flask were added 12.52 g (50 mmol) of ditrimethylolpropane (manufactured by Tokyo Kasei Kogyo Co., Ltd.), 41.62 g (210 mmol) of cis,cis-cyclohexane-1,2,4-tricarboxylic acid-1,2-anhydride (manufactured by Mitsubishi Gas Chemical Company, Inc., H-TMAn-S (trade name)), 6.10 g (50 mmol) of 4-dimethylaminopyridine, 22.26 g of triethylamine, and 150 g of dichloromethane, and the mixture was stirred at room temperature (25° C.) for 9 hours.

To the reaction solution were added 200 mL of 10% hydrochloric acid and 200 mL of methyl ethyl ketone, and the mixture was transferred to a separation funnel, washed with 100 mL of 10% hydrochloric acid twice, with 150 mL of saturated saline twice, dried over magnesium sulfate, and evaporated. Vacuum drying was performed at 120° C. to obtain 44.00 g of a white solid. As a result of $^1$H-NMR measurement, the obtained white solid was confirmed to be a compound (A-2) represented by the formula (17).

Figure 4:
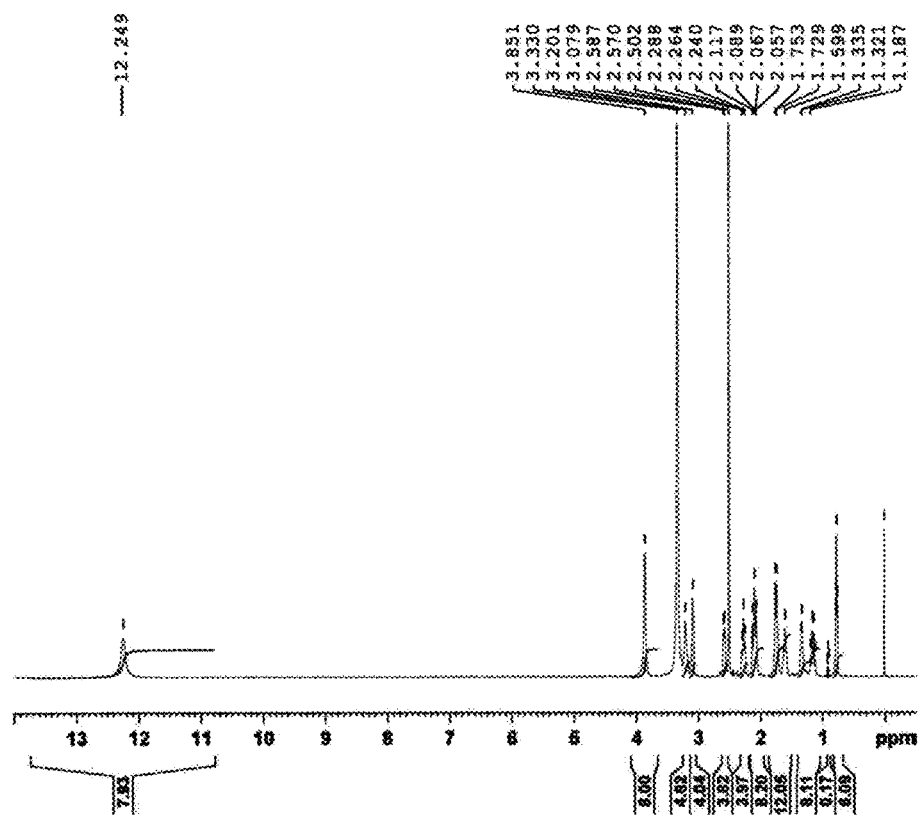
FIG. 4 is a $^1$H-NMR chart of a compound (A-2) obtained in Example 2.

The $^1$H-NMR attribution of the compound (A-2) is shown below. The $^1$H-NMR chart is shown in FIG. 4.

$^1$H-NMR (500 MHz, DMSO-d6) δ (ppm): 12.25 (s, 8H, —COOH), 3.85 (s, 8H), 3.20 (s, 4H), 3.08 (s, 4H), 2.58 (m, 4H), 2.26 (t, 4H), 2.09 (m, 8H), 1.74 (m, 8H), 1.60 (m, 4H), 1.33 (m, 4H), 1.15 (m, 4H), 0.78 (t, 6H)

In addition, the GPC area fraction (content) of the compound (A-2) contained in the reaction solution obtained above was calculated under the same conditions as in the GPC measurement described in the synthesis of the compound represented by the formula (16). As a result, the content was 88%.

Example 3

A compound (A-2) was synthesized as follows.

To a 200 mL flask were added 7.51 g (30 mmol) of ditrimethylolpropane (manufactured by Tokyo Kasei Kogyo Co., Ltd.), 23.78 g (120 mmol) of cis,cis-cyclohexane-1,2,4-tricarboxylic acid-1,2-anhydride (manufactured by Mitsubishi Gas Chemical Company, Inc., H-TMAn-S (trade name)), and 31.29 g of propylene glycol monomethyl ether acetate (manufactured by FUJIFILM Wako Pure Chemical Corporation, Wako first grade), and the mixture was stirred at 100° C. for 7 hours under a nitrogen atmosphere. Thereafter, the mixture was cooled to room temperature (25° C.) to obtain a reaction solution.

As a result of $^1$H-NMR measurement of the obtained reaction solution, it was confirmed that the compound (A-2) represented by the formula (17) was contained.

In addition, the obtained reaction solution was subjected to GPC measurement under the same conditions as the GPC measurement described in the synthesis of the compound represented by the formula (16). As a result, the disappearance of the peak derived from ditrimethylolpropane and the peak derived from cis,cis-cyclohexane-1,2,4-tricarboxylic acid-1,2-anhydride were confirmed. As a result of calculating the GPC area fraction (content) of the compound (A-2) contained in the reaction solution, the content was 82%.

Example 4

A compound A-2 was synthesized as follows.

To a 200 mL flask were added 7.51 g (30 mmol) of ditrimethylolpropane (manufactured by Tokyo Kasei Kogyo Co., Ltd.), 23.78 g (120 mmol) of cis,cis-cyclohexane-1,2,4-tricarboxylic acid-1,2-anhydride (manufactured by Mitsubishi Gas Chemical Company, Inc., H-TMAn-S (trade name)), and 31.29 g of butyl acetate (manufactured by FUJIFILM Wako Pure Chemical Corporation, reagent special grade), and the mixture was stirred at 100° C. for 6 hours under a nitrogen atmosphere. Thereafter, the mixture was cooled to room temperature (25° C.) to obtain a reaction solution.

As a result of $^1$H-NMR measurement of the obtained reaction solution, it was confirmed that the compound (A-2) represented by the formula (17) was contained.

In addition, the obtained reaction solution was subjected to GPC measurement under the same conditions as the GPC measurement described in the synthesis of the compound represented by the formula (16). As a result, the disappearance of the peak derived from ditrimethylolpropane and the peak derived from cis,cis-cyclohexane-1,2,4-tricarboxylic acid-1,2-anhydride was confirmed. As a result of calculating the GPC area fraction (content) of the compound (A-2) contained in the reaction solution, the content was 77%.

Example 5

A compound A-2 was synthesized as follows.

To a 200 mL flask were added 7.51 g (30 mmol) of ditrimethylolpropane (manufactured by Tokyo Kasei Kogyo Co., Ltd.), 23.78 g (120 mmol) of cis,cis-cyclohexane-1,2,4-tricarboxylic acid-1,2-anhydride (manufactured by Mitsubishi Gas Chemical Company, Inc., H-TMAn-S (trade name)), and 31.29 g of γ-butyrolactone (manufactured by FUJIFILM Wako Pure Chemical Corporation, Wako special grade), and the mixture was stirred at 100° C. for 7 hours under a nitrogen atmosphere. Thereafter, the mixture was cooled to room temperature (25° C.) to obtain a reaction solution.

As a result of $^1$H-NMR measurement of the obtained reaction solution, it was confirmed that the compound (A-2) represented by the formula (17) was contained.

The obtained reaction solution was subjected to GPC measurement under the same conditions as the GPC measurement described in the synthesis of the compound represented by the formula (16). As a result, the disappearance of the peak derived from ditrimethylolpropane and the peak derived from cis,cis-cyclohexane-1,2,4-tricarboxylic acid-1,2-anhydride was confirmed. As a result of calculating the GPC area fraction (content) of the compound (A-2) contained in the reaction solution, the content was 86%.

Example 6

A compound A-2 was synthesized as follows.

To a 200 mL flask were added 7.51 g (30 mmol) of ditrimethylolpropane (manufactured by Tokyo Kasei Kogyo Co., Ltd.), 23.78 g (120 mmol) of cis,cis-cyclohexane-1,2,4-tricarboxylic acid-1,2-anhydride (manufactured by Mitsubishi Gas Chemical Company, Inc., H-TMAn-S (trade name)), and 31.29 g of methyl ethyl ketone (manufactured by FUJIFILM Wako Pure Chemical Corporation, for organic synthesis, ultra-dehydrated), and the mixture was stirred at 80° C. for 15 hours under a nitrogen atmosphere. Thereafter, the mixture was cooled to room temperature (25° C.) to obtain a reaction solution.

As a result of $^1$H-NMR measurement of the obtained reaction solution, it was confirmed that the compound (A-2) represented by the formula (17) was contained.

In addition, the obtained reaction solution was subjected to GPC measurement under the same conditions as the GPC measurement described in the synthesis of the compound represented by the formula (16). As a result, the peak derived from ditrimethylolpropane and the peak derived from cis, cis-cyclohexane-1,2,4-tricarboxylic acid-1,2-anhydride were confirmed, and it was confirmed that these compounds remained in the reaction solution. As a result of calculating the GPC area fraction (content) of the compound (A-2) contained in the reaction solution, the content was 53%.

[Evaluation of Raw Material]
[Transmittance and Absorbance]

As the compound (A), the compound (A-1) obtained in Example 1 was used to prepare a solution of N-methylpyrrolidone containing 1% by mass of the compound (A-1), and measurement of the transmittance at each of a wavelength of 365 nm and a wavelength of 405 nm was carried out using an UV-vis measuring apparatus (Hitachi Spectrophotometer U-4100 manufactured by Hitachi High-Technologies Corporation).

Similarly, the compound (A-2) obtained in Example 2 was used as the compound (A), and the absorbance at each of wavelengths 365 nm and 405 nm was measured.

As the bismaleimide compound (B), MIZ-001 (trade name, mass average molecular weight (Mw): 3000) manufactured by Nippon Kayaku Co., Ltd. was used to prepare a chloroform solution containing this MIZ-001 (product name) at 1% by mass, and measurement of the transmittance at each of a wavelength of 365 nm and a wavelength of 405 nm was carried out using an UV-vis measuring apparatus (Hitachi Spectrophotometer U-4100 (product name) manufactured by Hitachi High-Technologies Corporation).

As the photo initiator (D), bis(2,4,6-trimethylbenzoyl)-phenylphosphine oxide (Omnirad® 819 (trade name) manufactured by IGM Resins B.V.) was used to prepare a chloroform solution containing this Omnirad® 819 (trade name) at 0.01% by mass, and measurement of the absorbance at each of a wavelength of 365 nm and a wavelength of 405 nm was carried out using an UV-vis measuring apparatus (U-4100 (trade name)).

The results are shown in Table 1.

TABLE 1

| | | Transmittance at 365 nm [%] | Transmittance at 405 nm [%] | Absorbance at 365 nm [—] | Absorbance at 405 nm [—] |
|---|---|---|---|---|---|
| Compound (A) | compound (A-1) obtained in Example 1 | 99 | 99 | — | — |
| | compound (A-2) obtained in Example 2 | 99 | 99 | — | — |
| Bismaleimide compound (B) | MIZ-001 | 19 | 88 | — | — |
| Photo initiator (D) | Omnirad819 | — | — | 0.32 | 0.18 |

Example 7

[Fabrication of Resin Composition and Resin Sheet]

A varnish (resin composition) was obtained by mixing 7.5 parts by mass of the compound (A-1) obtained in Example 1 as the compound (A), 60 parts by mass of MIZ-001 (trade name, mass average molecular weight (Mw): 3000) manufactured by Nippon Kayaku Co., Ltd. as the bismaleimide compound (B), 25 parts by mass of BCPH13 manufactured by Gun Ei Chemical Industry Co., Ltd. as the maleimide compound (C), 15 parts by mass of TMDM as the maleimide compound (C), and 5 parts by mass of bis(2,4,6-trimethylbenzoyl)-phenylphosphine oxide (Omnirad® 819 (trade name) manufactured by IGM Resins B.V.) as the photo initiator (D), and adding 168.8 parts by mass of methyl ethyl ketone (manufactured by Idemitsu Kosan Company, Ltd.) to the mixture, and heating and stirring using a 70° C. hot water bath. This varnish was dropped onto a 38 μm-thick PET-film (UNIPEEL® TR1-38 (trade name) manufactured by Unitika Ltd.), and a coating film was formed by spin coating (10 seconds in 300 rpm and then 30 seconds in 1000 rpm). The obtained coating film was dried at 90° C. for 5 minutes to obtain a resin sheet having a thickness of 10 μm using a PET film as a support.

(Fabrication of Resin for Evaluation)

The resin surfaces of the obtained resin sheets were pasted together, and a vacuum laminator (manufactured by Nikko-Materials Co., Ltd.) was used to perform vacuum drawing (5.0 hPa or less) for 30 seconds, followed by lamination molding at a pressure of 10 kgf/cm$^2$ and a temperature of 70° C. for 30 seconds. Furthermore, by performing lamination molding at a pressure of 7 kgf/cm$^2$ and a temperature of 70° C. for 60 seconds, a resin for evaluation with supports on both surfaces was obtained.

(Fabrication of Inner Layer Circuit Substrate)

After forming an inner layer circuit in a BT (bismaleimide triazine) resin laminate with a glass cloth base material, both surfaces of which are copper clad (copper foil thickness of 18 μm, thickness of 0.2 mm, CCL®-HL832NS (trade name) manufactured by Mitsubishi Gas Chemical Company, Inc.), both surfaces were subjected to roughening treatment for copper surfaces with CZ8100 (trade name) manufactured by MEC Co., Ltd., thereby obtaining an inner layer circuit substrate.

(Fabrication of Laminate for Evaluation)

The resin surface of the obtained resin sheet was disposed on the copper surface (one surface) of the inner layer circuit substrate described above, and a vacuum laminator (manufactured by Nikko-Materials Co., Ltd.) was used to perform vacuum drawing (5.0 hPa or less) for 30 seconds, followed by lamination molding at a pressure of 10 kgf/cm$^2$ and a temperature of 70° C. for 30 seconds. Furthermore, by performing lamination molding at a pressure of 10 kgf/cm$^2$ and a temperature of 70° C. for 60 seconds, a laminate for evaluation in which the inner layer circuit substrate, the resin layer and the support were laminated was obtained.

Example 8

A varnish and a resin sheet were obtained in the same manner as in Example 7, except that 7.5 parts by mass of compound (A-2) obtained in Example 2 was used instead of 7.5 parts by mass of compound (A-1) obtained in Example 1 as compound (A). Further, using the resin sheet, a resin for evaluation and a laminate for evaluation were obtained in the same manner as in Example 7.

Comparative Example 1

A varnish and a resin sheet were obtained in the same manner as in Example 7, except that 10 parts by mass of cis-4-cyclohexene-1,2-dicarboxylic acid anhydride (manufactured by Tokyo Kasei Kogyo Co., Ltd.) was used instead of 7.5 parts by mass of the compound (A-1) obtained in Example 1, and 168.8 parts by mass of methyl ethyl ketone was used in 172.5 parts by mass of methyl ethyl ketone. Further, using the resin sheet, a resin for evaluation and a laminate for evaluation were obtained in the same manner as in Example 7.

Comparative Example 2

A varnish and a resin sheet were obtained in the same manner as in Example 7, except that 10 parts by mass of ditrimethylolpropane (manufactured by Tokyo Kasei Kogyo Co., Ltd.) was used instead of 7.5 parts by mass of the compound (A-1) obtained in Example 1, and 168.8 parts by mass of methyl ethyl ketone was used in 172.5 parts by mass of methyl ethyl ketone. Further, using the resin sheet, a resin for evaluation and a laminate for evaluation were obtained in the same manner as in Example 7.

[Evaluation]

The resins for evaluation and the laminates for evaluation, which had been obtained in Examples and Comparative Examples, were measured and evaluated in accordance with the following methods. The results are shown in Table 2 and FIG. 5.

<Photocurability>

By using a photo DSC (DSC-2500 (brand name) manufactured by TA Instruments Japan Inc.) equipped with a light source (Omnicure® 52000 (trade name) manufactured by U-VIX Corporation) that is capable of being irradiated with an active energy ray including a wavelength of 200 to 600 nm, the obtained resin for evaluation was irradiated with an active energy ray including a wavelength of 200 to 600 nm at an illuminance of 30 mW and for an exposure time of 3.5 minutes, thereby obtaining a graph of time (sec) on the horizontal axis and heat flow (mW) on the vertical axis.

A graph of time (sec) on the horizontal axis and heat flow (mW) on the vertical axis was obtained under the same conditions as described above except that a filter for a ray with a wavelength of 405 nm (h-line) was used, and an active energy ray including a wavelength of 405 nm (h-line) was used.

In each graph, the enthalpy (J/g) was defined as the peak area when a line was drawn horizontally from the endpoint of the graph. The curability was evaluated in accordance with the following criteria.

"AA": enthalpy was 1 (J/g) or more.
"CC": enthalpy was less than 1 (J/g).

Note that an enthalpy of 1 (J/g) or more means that the curing of the resin is sufficiently advanced by exposure at a predetermined wavelength.

<Alkaline Developability>

Using a light source capable of applying an active energy ray including a wavelength of 405 nm (h-line) (MA-20 (product name) manufactured by MIKASA CO., LTD), the obtained laminate for evaluation was irradiated from above the support at an irradiation amount of 300 mJ/cm$^2$ to expose a half of the resin layer while the other half is unexposed. Thereafter, the support (PET film) was peeled, and the laminate was shaken in aqueous 2.38% TMAH (tetramethylammonium hydroxide) solution (developing solution, manufactured by Tokuyama Corporation) for 180 seconds. At this time, the developability was confirmed by shaking for 90 seconds, and shaking was performed for another 90 seconds if there was any undissolved residue. The alkali developability was visually evaluated according to the following criteria.

"AA": the exposed portion is not dissolved, and the unexposed portion is dissolved by shaking for 90 seconds.
"AB": the exposed portion is not dissolved, and the unexposed portion is dissolved by shaking for 180 seconds.
"BB": the exposed portion is not dissolved, and the unexposed portion is partially dissolved by shaking for 180 seconds.
"CC": either the exposed portion or the unexposed portion is not dissolved.

Figure 5:
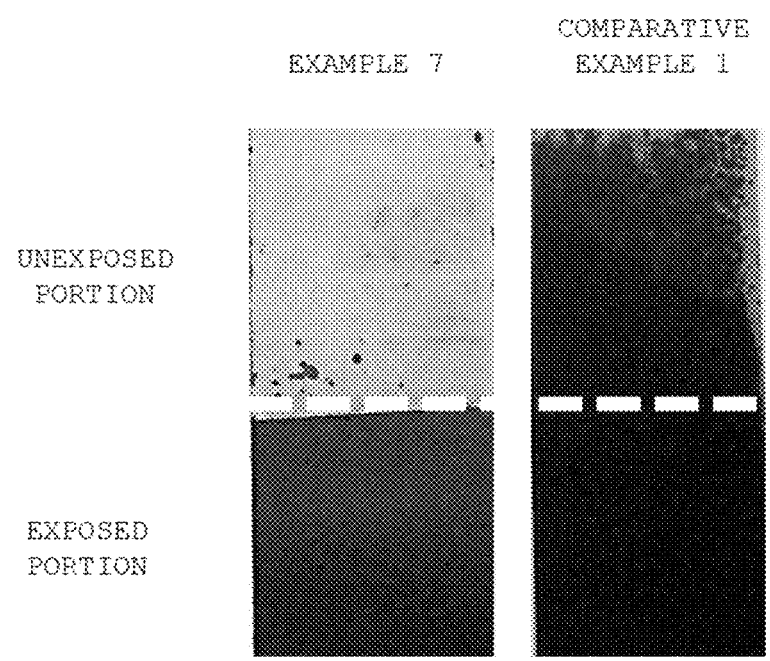
FIG. 5 shows photographs after alkaline development performed with the use of resin sheets obtained using an active energy ray including a wavelength of 405 nm (h-line) in Example 7 and Comparative Example 1.

FIG. 5 shows photographs after alkaline development performed with the use of the resin sheets which were obtained in Example 7 and Comparative Example 1.

TABLE 2

| | | Example 7 | Example 8 | Comparative Example 1 | Comparative Example 2 |
|---|---|---|---|---|---|
| Compound (A) | compound (A-1) obtained in Example 1 | 7.5 | | | |
| | compound (A-2) obtained in Example 2 | | 7.5 | | |
| Compound | cis-4-cyclohexene-1,2-dicarboxylic acid anhydride | | | 10 | |
| | ditrimethylolpropane | | | | 10 |
| Bismaleimide compound (B) | MIZ-001 | 60 | 60 | 60 | 60 |
| Maleimide compound (C) | BCPH13 | 25 | 25 | 25 | 25 |
| | TMDM | 15 | 15 | 15 | 15 |
| Photo initiator (D) | Omnirad819 | 5 | 5 | 5 | 5 |
| Evaluation | photocurability (405 nm) | AA | AA | AA | AA |
| | photocurability (200-600 nm) | AA | AA | AA | AA |
| | alkaline developability | AB | AA | BB | CC |

Table 2 reveals that according to the present embodiment, exposure with any of an active energy ray including a wavelength of 405 nm (h-line) and an active energy ray including a wavelength of 200 to 600 nm ensures that the resin composition is properly light-sensitive and can be photocured. According to the present embodiment, a cured product having excellent alkaline developability can be obtained.

The present application is based on Japanese Patent Application No. 2019-223931 filed on Dec. 11, 2019, the contents of which are incorporated herein by reference.

INDUSTRIAL APPLICABILITY

The resin composition of the present embodiment does not inhibit a photocuring reaction in the exposure step and is capable of imparting excellent alkaline developability in the development step in the production of a multilayer printed wiring board, and therefore industrially useful, and can be used for applications including, for example, a photosensitive film, a photosensitive film with a support, a prepreg, a resin sheet, a circuit substrate (applications for a laminate, applications for a multilayer printed wiring board, and the like), a solder resist, an underfill material, a die bonding material, a semiconductor sealing material, a hole filling resin, and a component embedding resin.

The invention claimed is:

1. A compound represented by the following formula (17):

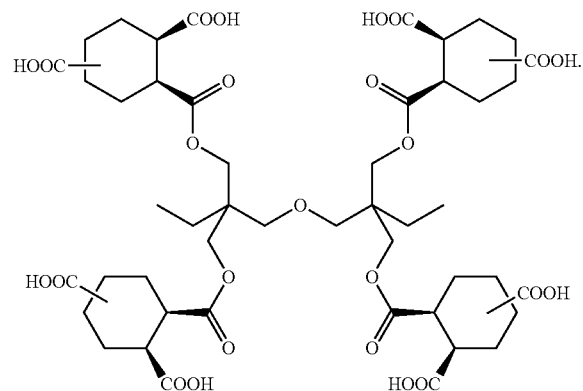

2. A method for producing the compound according to claim 1, comprising a step of reacting an alcohol compound represented by the following formula (4) with an acid anhydride represented by the following formula (6):

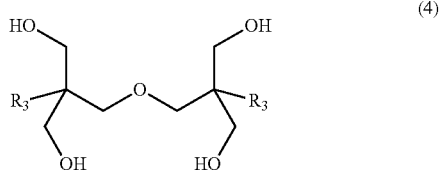

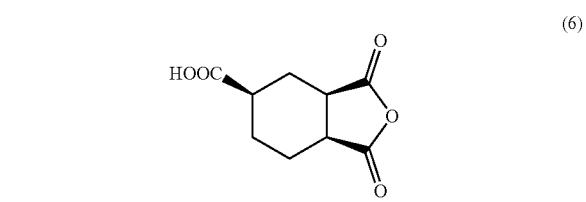

wherein each $R_3$ independently represents an ethyl group.

3. The production method according to claim 2, wherein the reaction is carried out in the absence of a catalyst.

4. The production method according to claim 2, wherein the reaction is performed in at least one solvent selected from the group consisting of a halogen solvent, a ketone solvent, and an ester solvent.

5. The production method according to claim 4, wherein the solvent is at least one selected from the group consisting of dichloromethane, methyl ethyl ketone, butyl acetate, γ-butyrolactone, and propylene glycol monomethyl ether acetate.

6. A resin composition comprising a compound represented by the following formula (16) and/or a compound represented by the following formula (17):

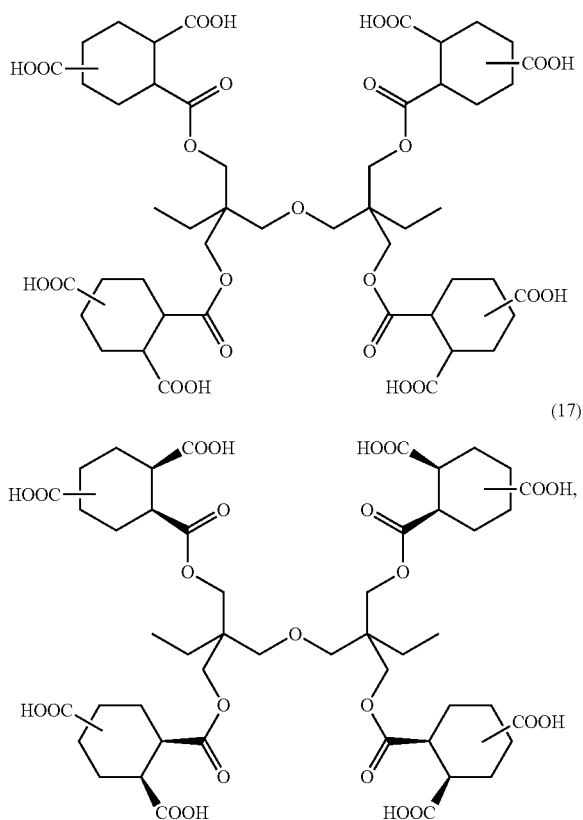

(16)

(17)

and a bismaleimide compound (B) comprising a constituent unit represented by the following formula (7) and maleimide groups at both ends of the molecular chain:

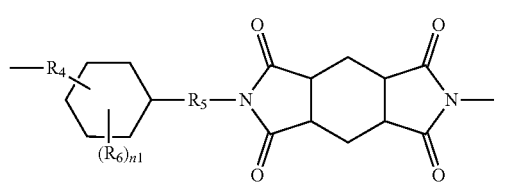

(7)

wherein $R_4$ represents a linear or branched alkylene group having 1 to 16 carbon atoms, or a linear or branched alkenylene group having 2 to 16 carbon atoms; $R_5$ represents a linear or branched alkylene group having 1 to 16 carbon atoms, or a linear or branched alkenylene group having 2 to 16 carbon atoms; each $R_6$ independently represents a hydrogen atom, a linear or branched alkyl group having 1 to 16 carbon atoms, or a linear or branched alkenyl group having 2 to 16 carbon atoms; and each $n_1$ independently represents an integer of 1 to 10.

7. The resin composition according to claim 6, further comprising at least one maleimide compound (C) selected from the group consisting of a compound represented by the following formula (8), a compound represented by the following formula (9), a compound represented by the following formula (10), a compound represented by the following formula (11), a compound represented by the following formula (12), and a compound represented by the following formula (13):

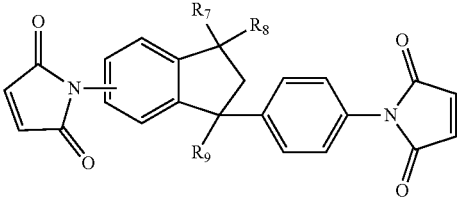

(8)

wherein $R_7$, $R_8$, and $R_9$ each independently represent a hydrogen atom, or a linear or branched alkyl group having 1 to 8 carbon atoms and optionally having a substituent;

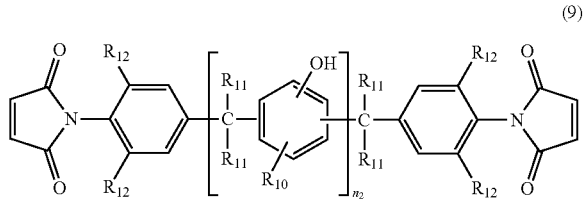

(9)

wherein $R_{10}$, $R_{11}$, and $R_{12}$ each independently represent a hydrogen atom, a hydroxyl group, or a linear or branched alkyl group having 1 to 6 carbon atoms and optionally having a substituent; and $n_2$ is an integer of 1 to 10;

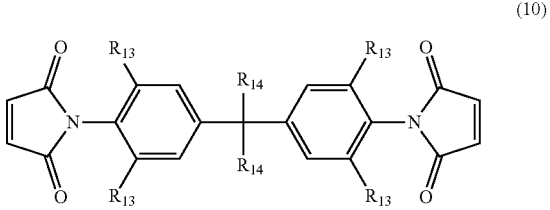

(10)

wherein each $R_{13}$ independently represents a hydrogen atom, a methyl group or an ethyl group, and each $R_{14}$ independently represents a hydrogen atom or a methyl group;

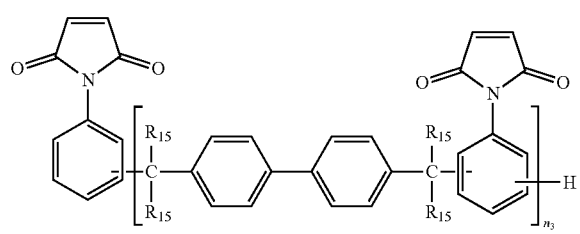

(11)

wherein each $R_{15}$ independently represents a hydrogen atom or a methyl group; and $n_3$ is an integer of 1 to 10;

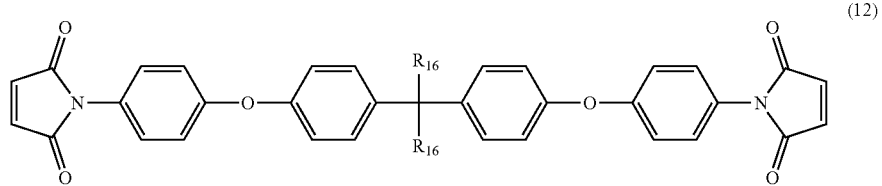

wherein each $R_{16}$ independently represents a hydrogen atom, a methyl group or an ethyl group; and

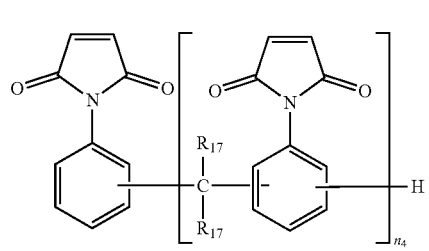

wherein each $R_{17}$ independently represents a hydrogen atom or a methyl group; and $n_4$ is an integer of 1 to 10.

8. The resin composition according to claim 6, further comprising a photo initiator (D).

9. The resin composition according to claim 8, wherein the photo initiator (D) comprises a compound represented by the following formula (14):

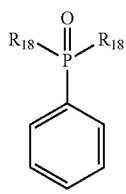

wherein each $R_{18}$ independently represents a group represented by the following formula (15) or a phenyl group; and

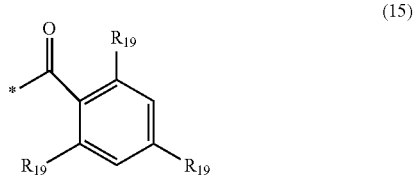

wherein -* represents a bonding hand, and each $R_{19}$ independently represents a hydrogen atom or a methyl group.

10. A resin sheet comprising:
a support; and
a resin layer disposed on one surface or both surfaces of the support,
wherein the resin layer comprises the resin composition according to claim 6.

11. The resin sheet according to claim 10, wherein the resin layer has a thickness of 1 to 50 μm.

12. A multilayer printed wiring board comprising:
an insulation layer; and
a conductor layer formed on one surface or both surfaces of the insulation layer,
wherein the insulation layer comprises the resin composition according to claim 6.

13. A semiconductor device comprising the resin composition according to claim 6.

* * * * *